US010064654B2

(12) United States Patent
Woodburn, Sr. et al.

(10) Patent No.: US 10,064,654 B2
(45) Date of Patent: Sep. 4, 2018

(54) FLEXIBLE MAXILLO-MANDIBULAR FIXATION DEVICE

(71) Applicant: DePuy Synthes Products, Inc., Raynham, MA (US)

(72) Inventors: William N. Woodburn, Sr., Middleton, NJ (US); William Griffith, Downingtown, PA (US); Jessica Regan Barber, West Chester, PA (US); Gregory Parranto, Naperville, IL (US)

(73) Assignee: Depuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/786,718

(22) Filed: Oct. 18, 2017

(65) Prior Publication Data

US 2018/0036036 A1    Feb. 8, 2018

Related U.S. Application Data

(63) Continuation of application No. 14/326,901, filed on Jul. 9, 2014, now Pat. No. 9,820,777.

(51) Int. Cl.

| | |
|---|---|
| *A61B 17/04* | (2006.01) |
| *A61B 17/84* | (2006.01) |
| *A61F 2/08* | (2006.01) |
| *A61B 17/64* | (2006.01) |
| *A61C 5/00* | (2017.01) |
| *A61B 17/80* | (2006.01) |

(52) U.S. Cl.
CPC ...... *A61B 17/6433* (2013.01); *A61B 17/8071* (2013.01); *A61B 17/8085* (2013.01); *A61C 5/007* (2013.01); *A61B 17/8057* (2013.01)

(58) Field of Classification Search
None
See application file for complete search history.

(56) References Cited

U.S. PATENT DOCUMENTS

| | | | |
|---|---|---|---|
| 1,638,006 | A | 8/1927 | Aderer |
| 1,797,481 | A | 3/1931 | Lewis |
| 2,481,177 | A | 9/1949 | Tofflemire |
| 2,502,902 | A | 4/1950 | Tofflemire |
| 2,580,821 | A | 1/1952 | Toufick |
| 3,474,779 | A | 10/1969 | Wall, Jr. |
| 4,230,104 | A | 10/1980 | Richter |

(Continued)

FOREIGN PATENT DOCUMENTS

| | | |
|---|---|---|
| EP | 0654250 A1 | 5/1995 |
| WO | 98/33448 A1 | 8/1998 |

(Continued)

*Primary Examiner* — Sameh Boles
(74) *Attorney, Agent, or Firm* — Baker & Hostetler LLP

(57) ABSTRACT

A system for achieving maxillo-mandibular fixation includes a bone fixation device including a bone fixation body formed from a plurality of links. The links define corresponding crests and valleys so as to impart flexibility into the bone fixation body. Thus, the bone fixation body can be aligned with the dental arch of the mandible and maxilla as necessary, and subsequently fastened to the underlying bone. Each bone fixation device includes at least one securement location on the fixation body that can attach to a securement device, such that the securement device fixes or stabilizes the mandible and the maxilla with respect to each other.

18 Claims, 17 Drawing Sheets

(56) References Cited

U.S. PATENT DOCUMENTS

| | | |
|---|---|---|
| 4,651,724 A | 3/1987 | Berentey et al. |
| 4,904,188 A | 2/1990 | Baurmash |
| 4,959,065 A | 9/1990 | Arnett et al. |
| 5,074,865 A | 12/1991 | Fahmy |
| 5,250,048 A | 10/1993 | Gundolf |
| 5,468,242 A | 11/1995 | Reisberg |
| D366,114 S | 1/1996 | Ohata |
| 5,690,631 A | 11/1997 | Duncan et al. |
| 5,752,958 A | 5/1998 | Wellisz |
| 5,779,707 A | 7/1998 | Bertholet et al. |
| 5,984,925 A | 11/1999 | Apgar |
| 6,086,365 A | 7/2000 | Fields |
| 6,093,188 A | 7/2000 | Murray |
| 6,106,544 A | 8/2000 | Brazeau |
| 6,120,288 A | 9/2000 | Deslauriers |
| 6,257,884 B1 | 7/2001 | Chang |
| 6,471,706 B1 | 10/2002 | Schumacher et al. |
| 9,107,716 B2 * | 8/2015 | Frigg ............... A61B 17/8071 |
| 2004/0030388 A1 | 2/2004 | Null et al. |
| 2004/0044345 A1 | 3/2004 | Demoss et al. |
| 2005/0192675 A1 | 9/2005 | Robinson |
| 2008/0255620 A1 | 10/2008 | Strauss et al. |
| 2009/0148804 A1 | 6/2009 | Marcus |
| 2010/0179552 A1 | 7/2010 | Wolter |
| 2011/0152951 A1 | 6/2011 | Baker |
| 2015/0297272 A1 | 10/2015 | Ghobadi et al. |

FOREIGN PATENT DOCUMENTS

| | | |
|---|---|---|
| WO | 99/05982 A1 | 2/1999 |
| WO | 2004/045389 A2 | 6/2004 |
| WO | 2009/055537 A1 | 4/2009 |
| WO | 2010/025263 A1 | 3/2010 |
| WO | 2010/062379 A1 | 6/2010 |
| WO | 2011/063368 A1 | 5/2011 |
| WO | 2014/031935 A1 | 2/2014 |

* cited by examiner

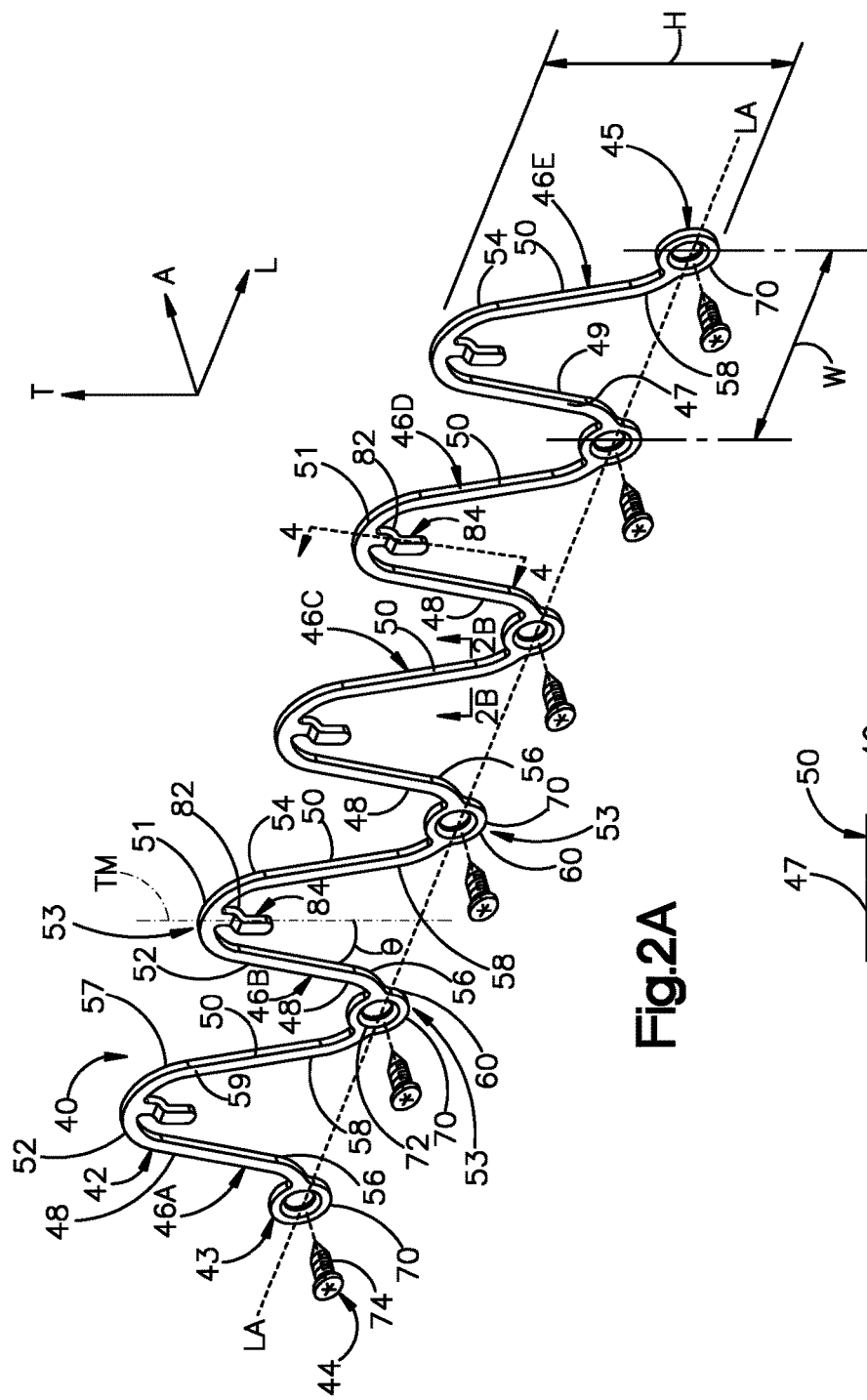
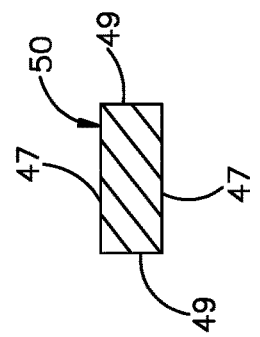
Fig.2A
Fig.2B

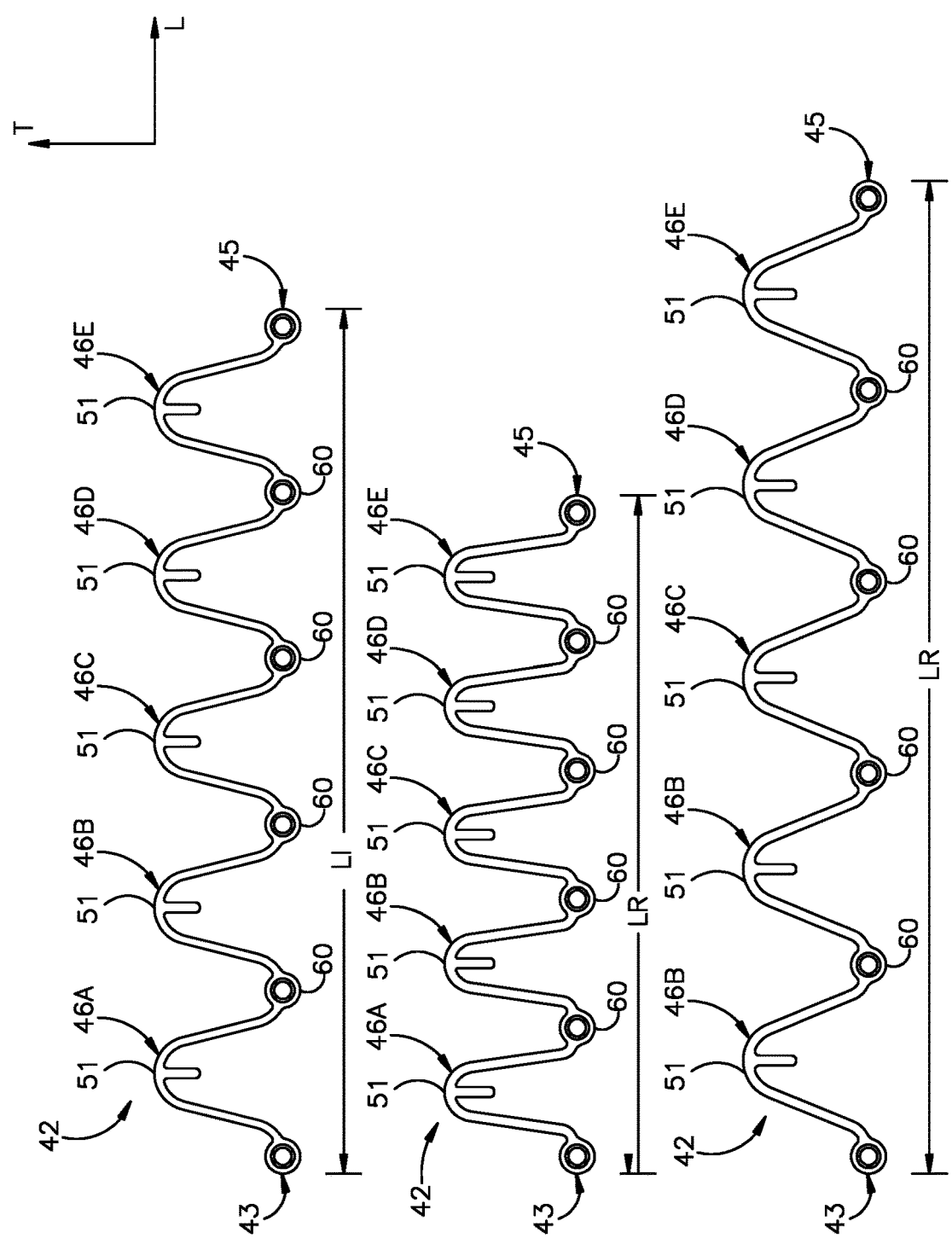

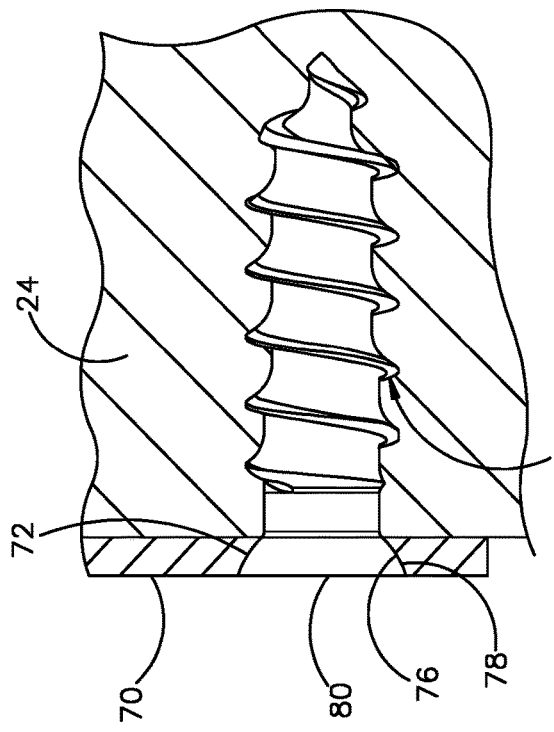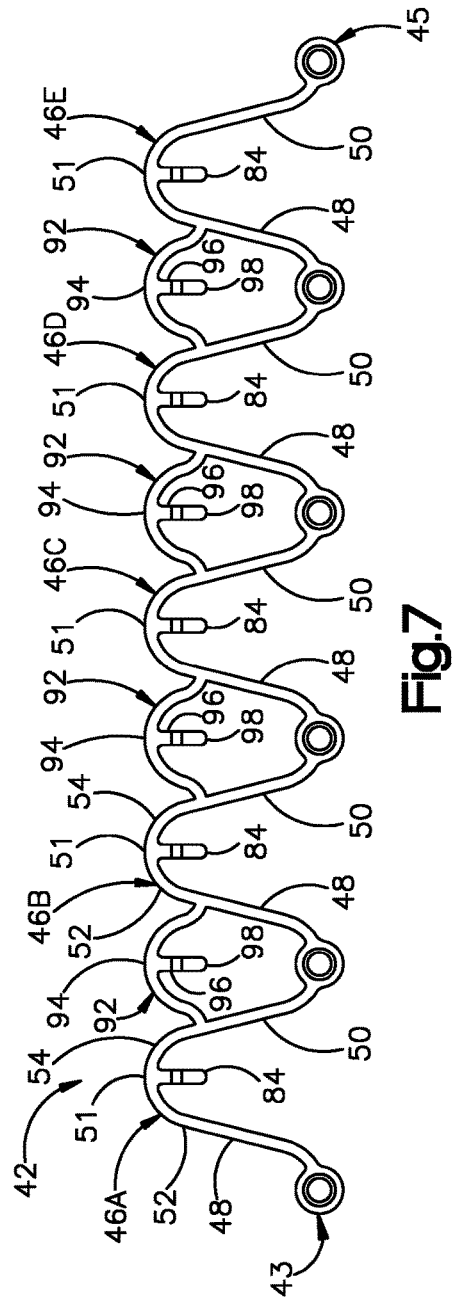

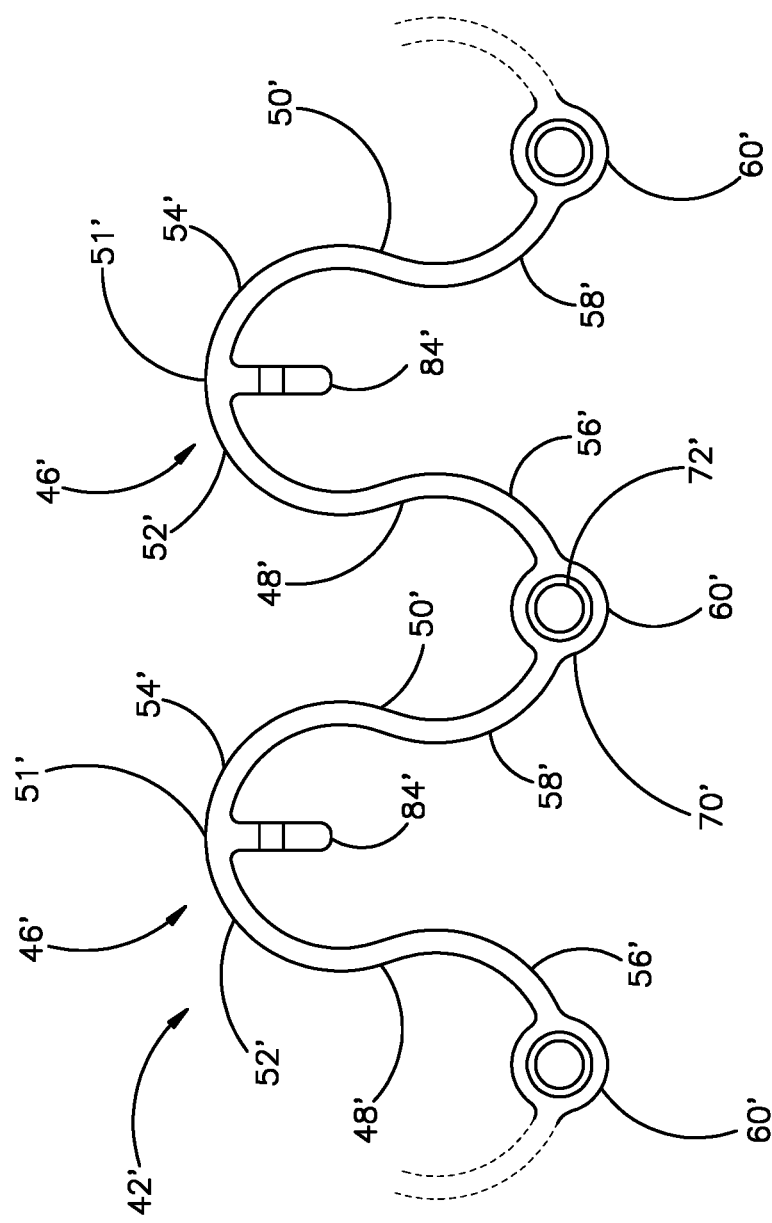

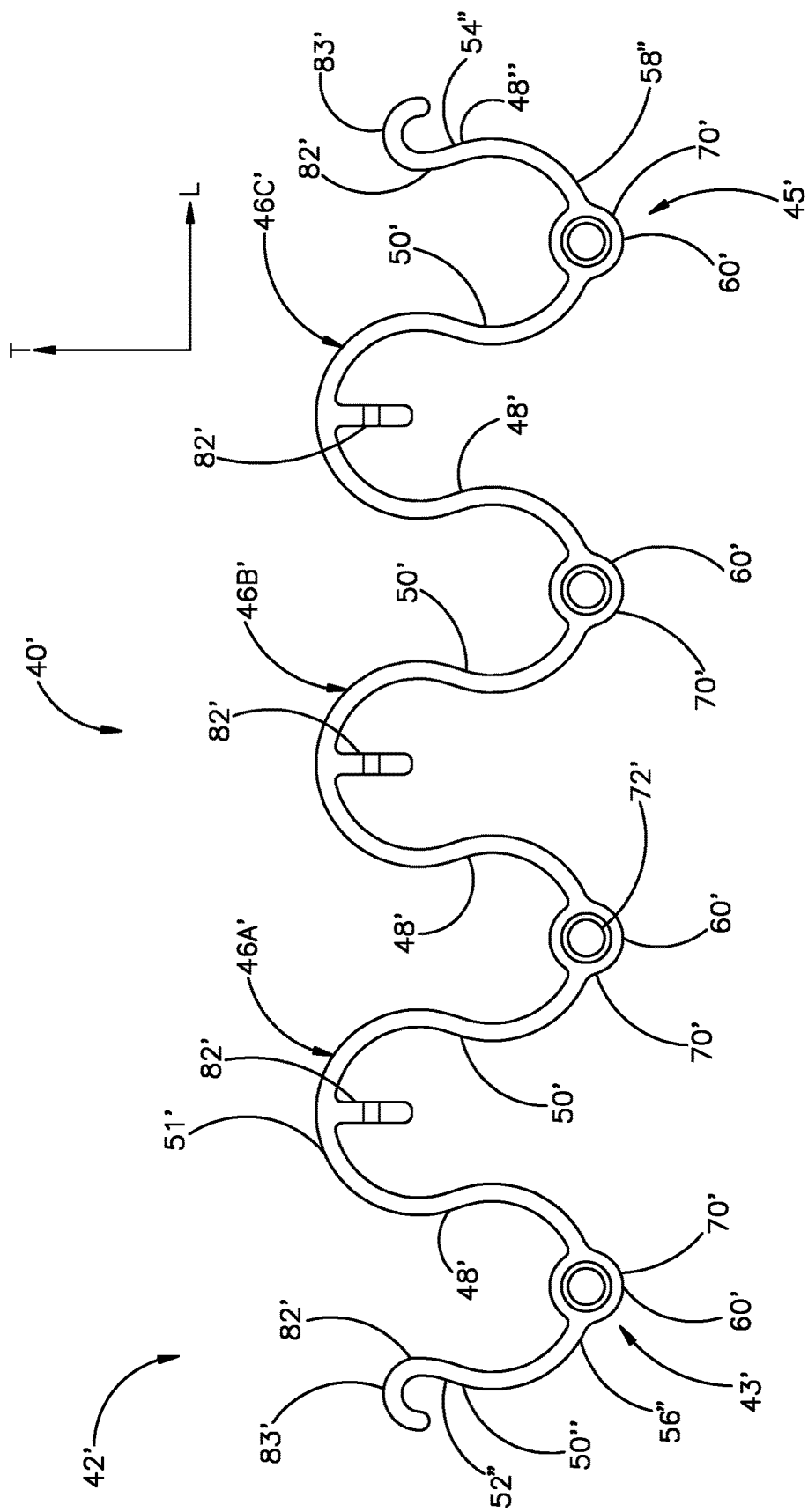

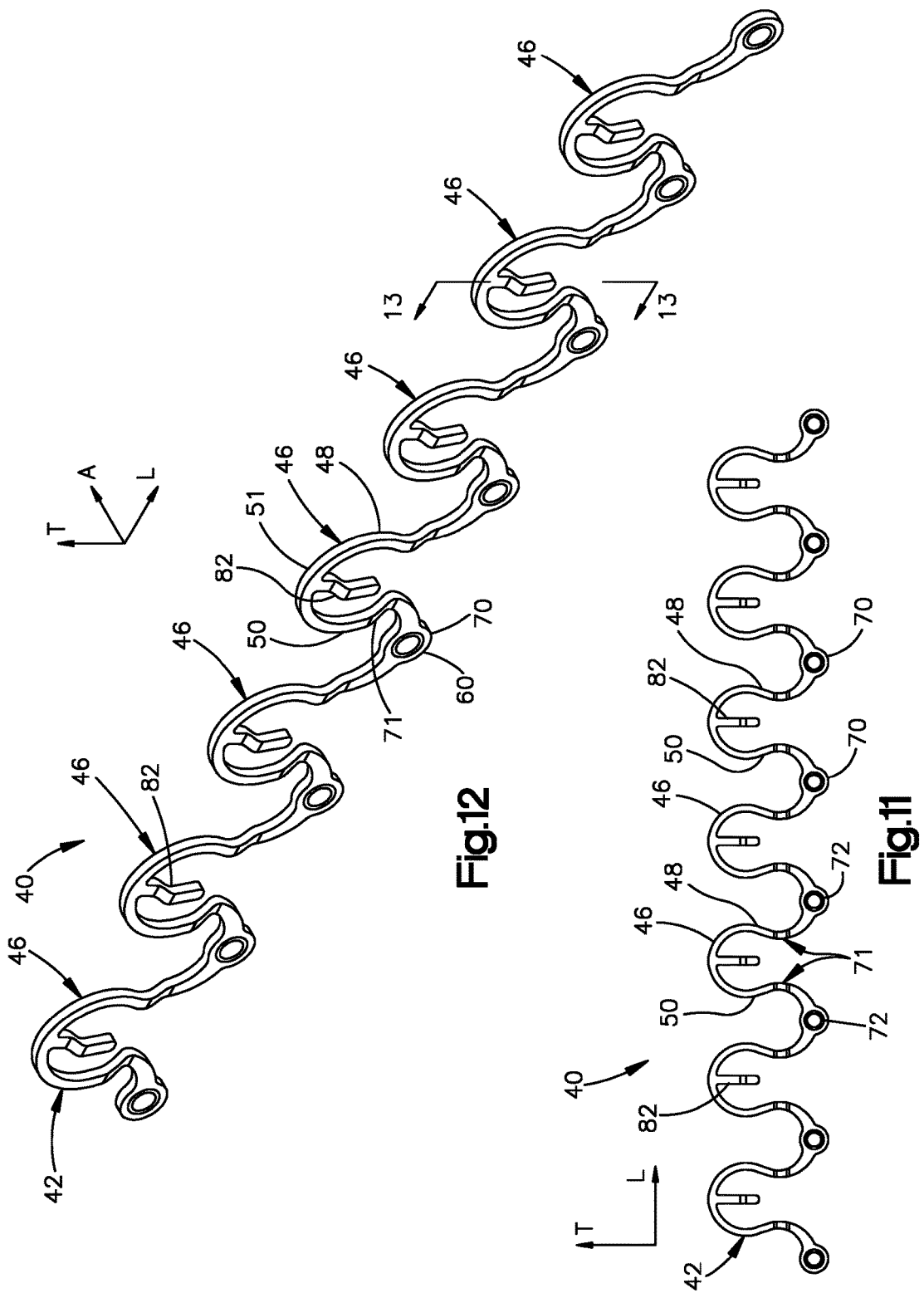

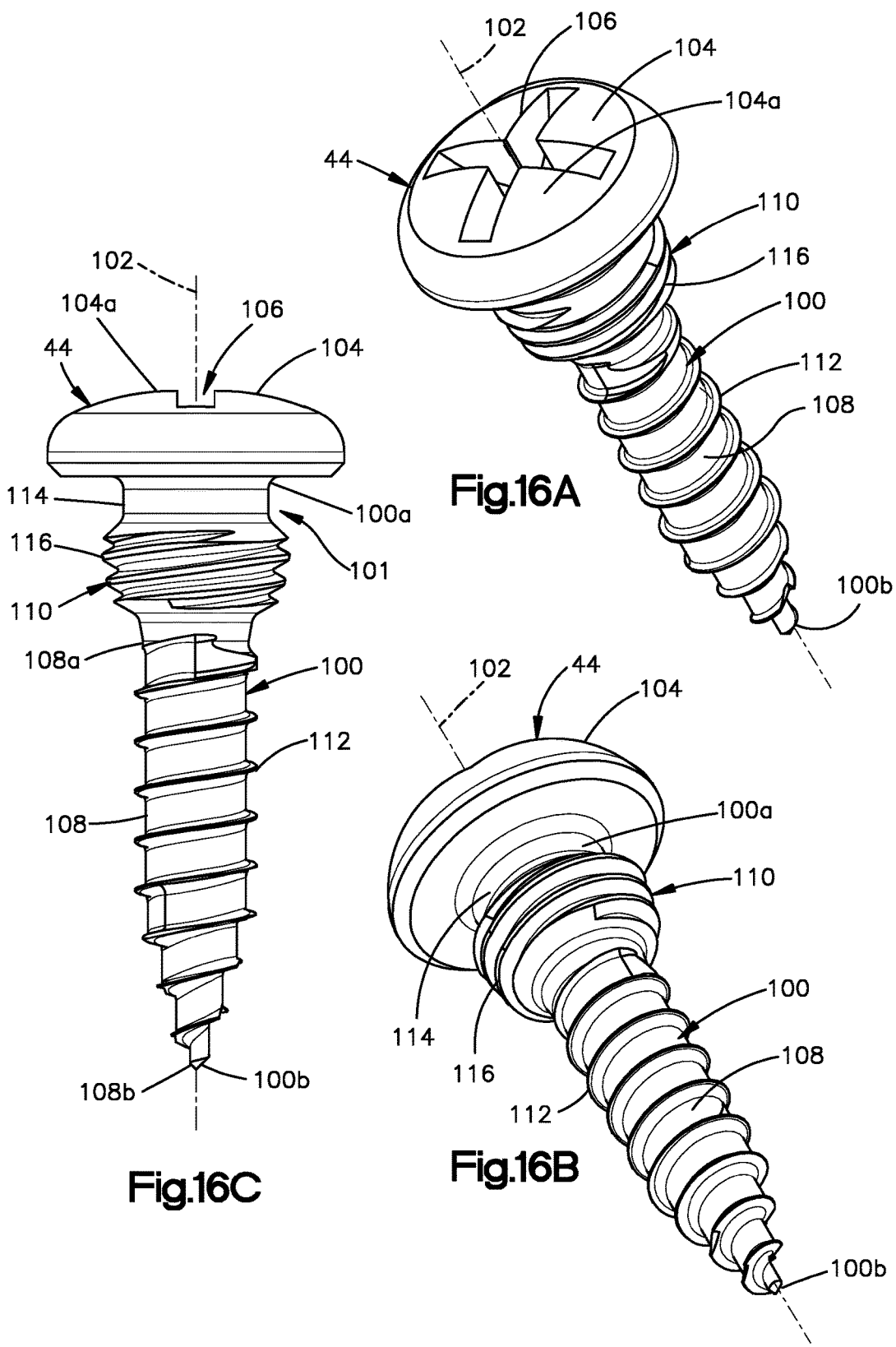

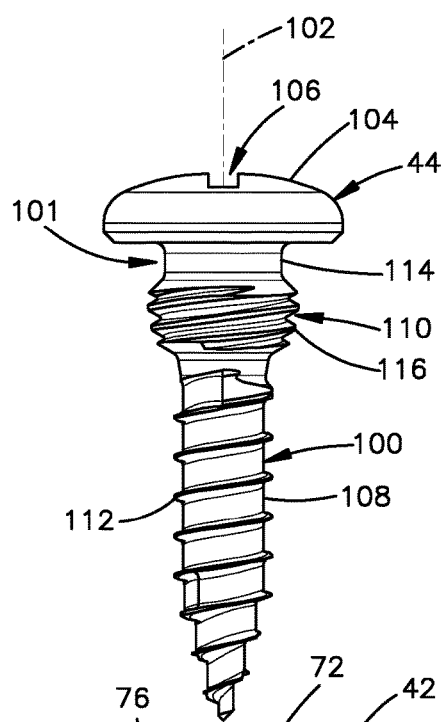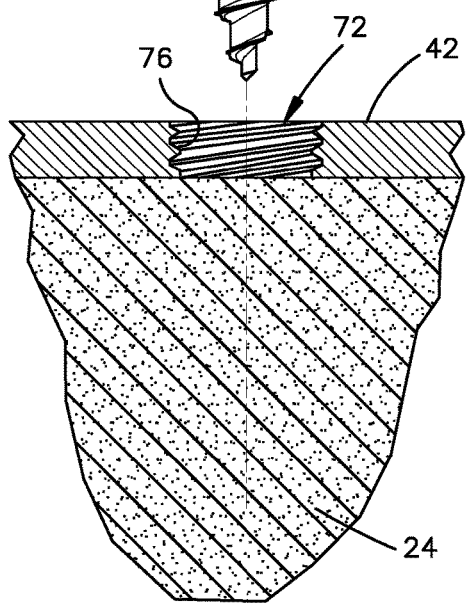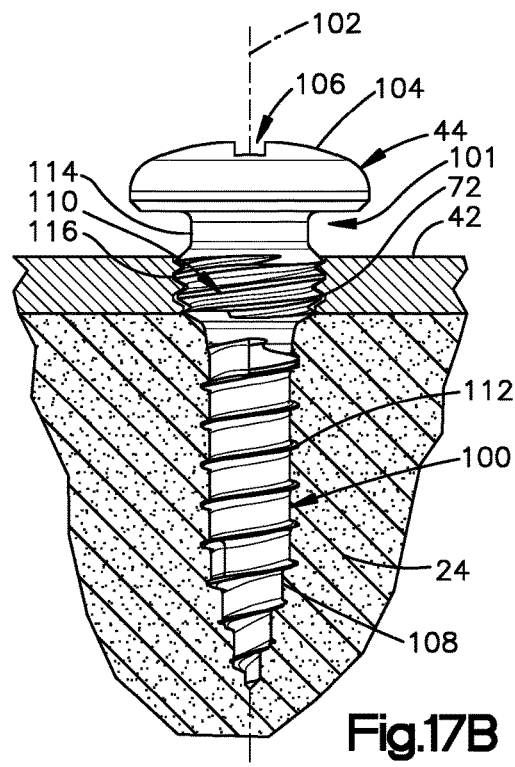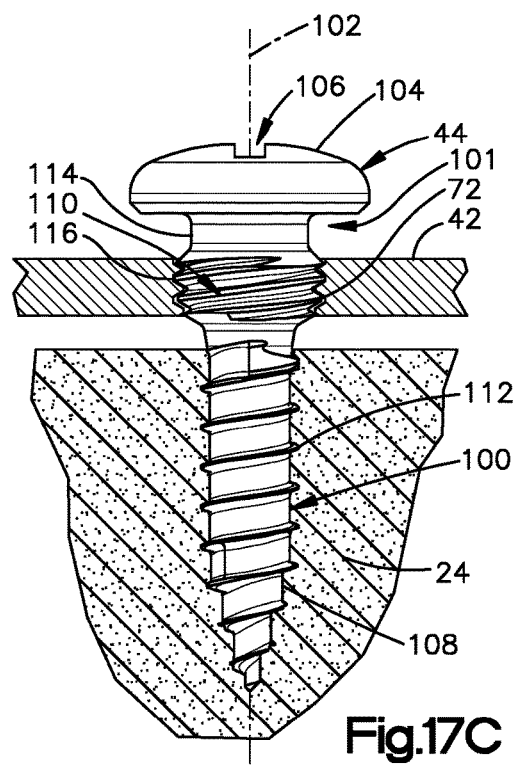
Fig.17A
Fig.17B
Fig.17C

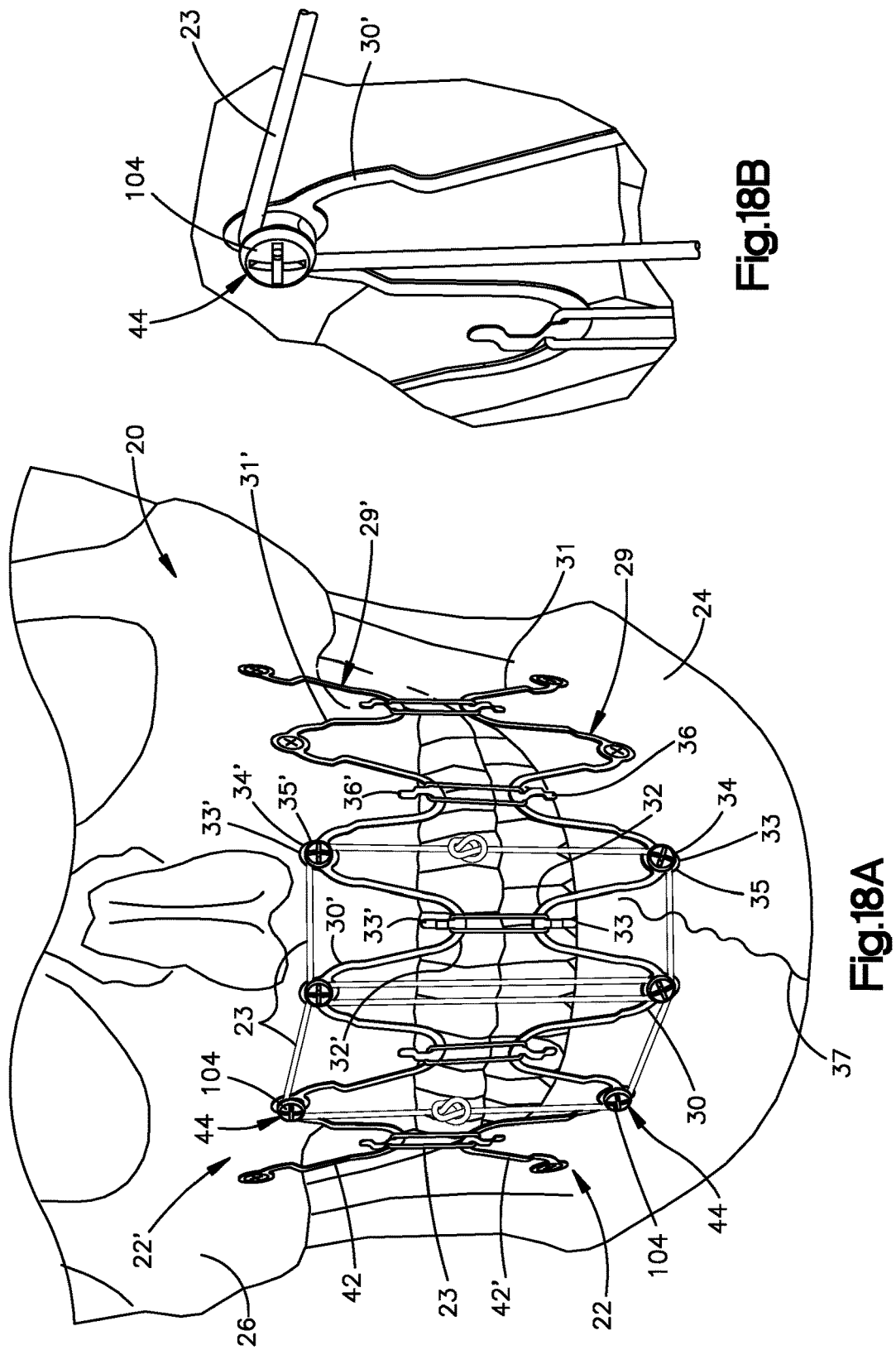

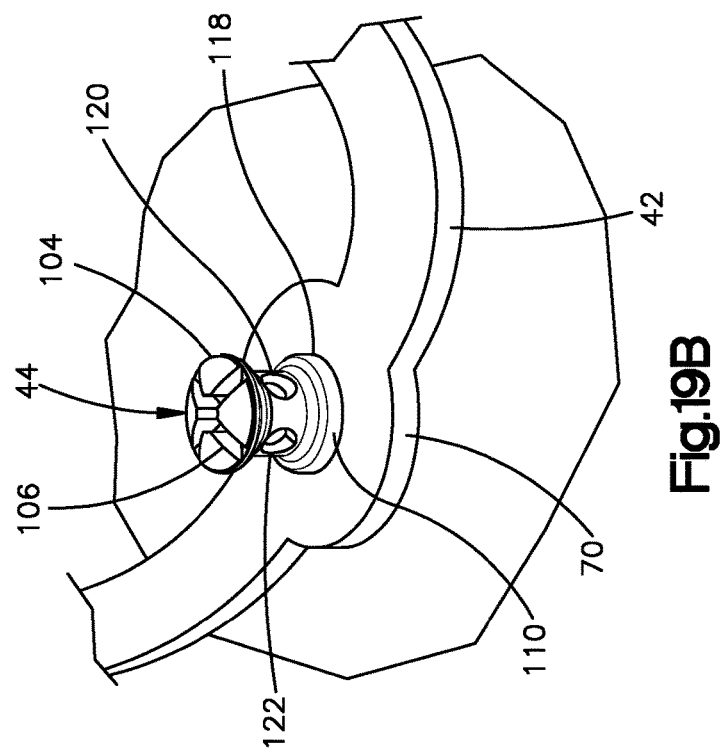
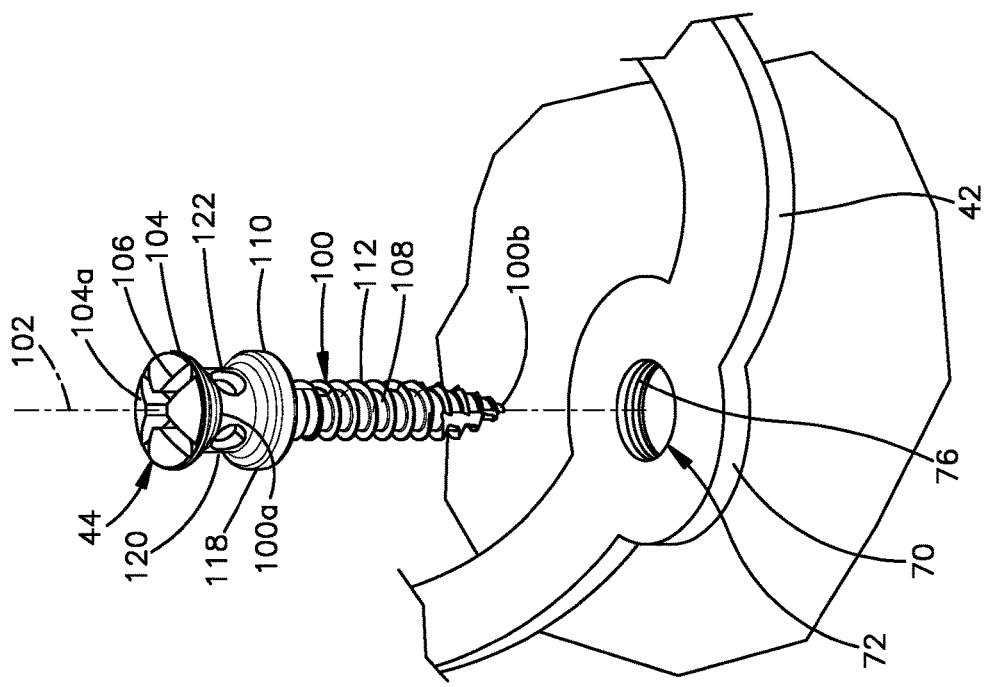

FLEXIBLE MAXILLO-MANDIBULAR FIXATION DEVICE

CROSS-REFERENCE TO RELATED APPLICATIONS

This application is a continuation of U.S. patent application Ser. No. 14/326,901, filed on Jul. 9, 2014, the disclosure of which is hereby incorporated by reference as if set forth in its entirety herein.

BACKGROUND

The fixation or stabilization of the upper and lower dental occlusal arches to each other is known as intermaxillary fixation (IMF) and also known as maxillo-mandibular fixation (MMF). MMF has historically been included in the treatment of fracture, orthognathic, and reconstructive jaw procedures. Various methods for achieving MMF are known in the art.

Circumdental wiring techniques include metallic wires that are placed around one or more teeth and then twisted in various methods to secure the teeth. Wires or twisted pairs of wires can form cables and be twisted to each other to stabilize the dental arch. Loops formed on mandibular teeth can be wired to loops formed around maxillary teeth in order to stabilize the top dentition to the bottom dentition. While the materials used in circumdental wiring are relatively inexpensive, the technique is tedious and time consuming. The wires also can interfere with dental hygiene.

Another conventional technique includes arch bars that are used in combination with wiring. Specifically, a metal bar is preformed to correspond with the curvature of the dental arch. Wires are then passed around the teeth and over the bar, and then twisted to the bar. This is performed at multiple locations along the bar to provide stability around the dental arch. Since the bars typically have bent or formed hooks on them for securing wire, the hooks can be used for wiring the upper arch bar to the lower arch bar. Elastic bands can also be used to fix the upper arch bar to the lower arch bar. Unfortunately, this technique is time consuming, and interferes with dental hygiene. Further, passing wires around the teeth and over the bar creates a risk that the surgeon may puncture his or her surgical glove, thereby potentially facilitating the spread of disease.

Another conventional technique involves placing a plurality of screws in the mandible or maxilla in regions that avoid the tooth roots. The screw heads may contain through holes. The screw head serves as an area around which wires may be wrapped, and the holes can facilitate the passage of wire through the heads. Thus, wires may be secured to adjoining sets of screws to provide MMF. This system unfortunately suffers from a lack of overall structural stability which can be necessary, for instance, when addressing fractures around the teeth.

SUMMARY

In accordance with one embodiment, a bone fixation system includes first and second bone fixation devices. The first bone fixation device includes a first fixation body having a first securement location and a first attachment location. The first bone fixation device also includes a bone fastener configured to be embedded into an underlying first bone at the first attachment location, thereby attaching the first fixation body to the first bone. The second bone fixation device includes a second fixation body having a second securement location and a second attachment location. The second bone fixation device also includes a bone fastener configured to be embedded into an underlying second bone at the second attachment location, thereby attaching the second fixation body to the second bone. The first and second securement locations are configured to engage with a securement device that secures the first and second bone fixation devices with respect to each other.

BRIEF DESCRIPTION OF THE DRAWINGS

The foregoing summary, as well as the following detailed description, is better understood when read in conjunction with the appended drawings. For the purpose of illustrating the maxillo-mandibular fixation device and related method thereof, there is shown in the drawings exemplary embodiments; however, the maxillo-mandibular fixation device and related methods are not limited to the specific embodiments and methods disclosed. Like reference numerals refer to corresponding parts throughout the several embodiments of the drawings, in which:

FIG. 2A is a perspective view of a bone fixation body constructed in accordance with one example embodiment in a neutral configuration;

FIG. 2B is a sectional elevation view of the fixation device illustrated in FIG. 2A taken along the line 2B-2B;

FIG. 3A is a front view of the fixation device illustrated in FIG. 2A in the neutral configuration;

FIG. 3B is a front view of the fixation device illustrated in FIG. 3A, but shown in a compressed configuration;

FIG. 3C is a front elevation view of the fixation device illustrated in FIG. 3A, but shown in an expanded configuration;

FIG. 6 is a sectional elevation view of the mandibular fixation device illustrated in FIG. 2A, implanted in the manner illustrated in FIG. 1, and taken along line 6-6 of FIG. 1 to show the fixation of the device to the mandible;

FIG. 7 is a front elevation view of a bone fixation body constructed in accordance with an alternative embodiment;

FIG. 8 is a front elevation view of a bone fixation body constructed in accordance with another alternative embodiment;

FIG. 9 is a front elevation view of a bone fixation body constructed in accordance with another alternative embodiment;

FIG. 11 is a front view of a bone fixation body of the fixation system illustrated in FIG. 10;

FIG. 12 is a perspective view of the bone fixation body of the fixation system illustrated in FIG. 11, shown in a relaxed configuration;

FIG. 16A is a perspective view of a fastener constructed in accordance with another embodiment;

FIG. 16B is another perspective view of the fastener illustrated in FIG. 16A;

FIG. 16C is a side elevation view of the fastener illustrated in FIG. 16A;

FIG. 17A is an exploded sectional side elevation view showing insertion of the fixation device illustrated in FIG. 14 into a screw hole of the fixation body illustrated in FIG. 12;

FIG. 17B is a sectional side elevation view showing the fixation device illustrated in FIG. 14 inserted into a screw hole of the fixation body illustrated in FIG. 12;

FIG. 17C is a sectional side elevation view showing the fixation device illustrated in FIG. 14 inserted into a screw hole of the fixation body illustrated in FIG. 12 in accordance with another embodiment;

FIG. 18A is a perspective view of the maxillo-mandibular fixation system as illustrated in FIG. 10, but wherein the fasteners are constructed as illustrated in FIG. 16A;

FIG. 18B is an enlarged perspective view of a portion of the maxillo-mandibular fixation system illustrated in FIG. 18A;

FIG. 19A is a perspective view showing insertion of a fixation member constructed in accordance with an alternative embodiment into a screw hole of the fixation body illustrated in FIG. 12;

FIG. 19B is a sectional side elevation view showing the fixation device illustrated in FIG. 19A inserted into a screw hole of the fixation body illustrated in FIG. 12.

DETAILED DESCRIPTION OF ILLUSTRATIVE EMBODIMENTS

Figure 1:
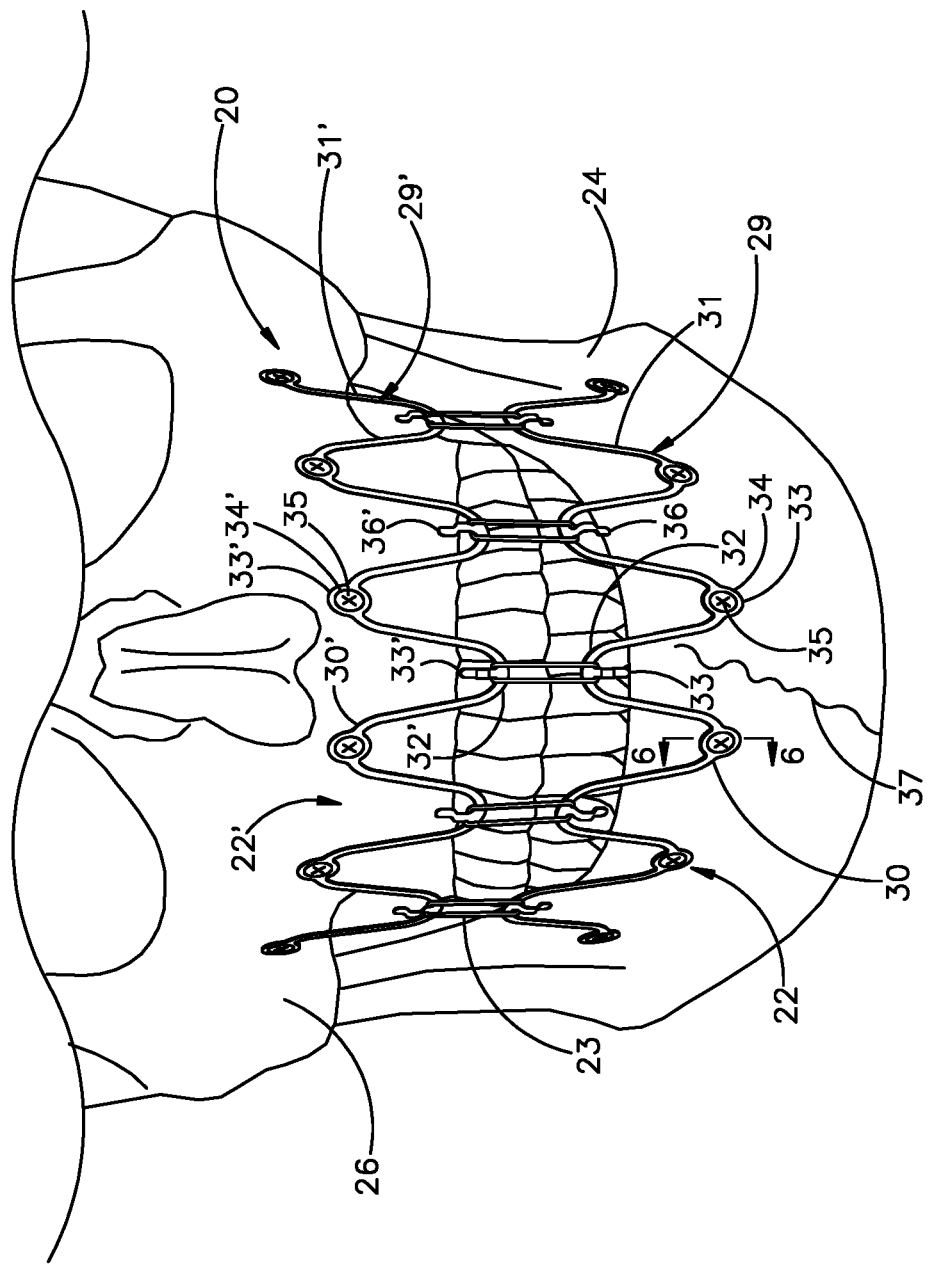
FIG. 1 is a perspective view of a maxillo-mandibular fixation system including a pair of fixation devices attached to the maxilla and mandible of a patient, and secured together.

For convenience, the same or equivalent elements in the various embodiments illustrated in the drawings have been identified with the same reference numerals. Certain terminology is used in the following description for convenience only and is not limiting. The words "right", "left", "upper," and "lower" designate directions in the drawings to which reference is made. The words "inward", "inwardly", "outward", "outwardly," "upward," "upwardly," "downward," and "downwardly" refer to directions toward and away from the geometric center of the device and/or designated parts thereof. The terminology intended to be non-limiting includes the above-listed words, derivatives thereof and words of similar import.

Referring initially to FIGS. 1 and 2A-B, a bone fixation, or stabilization, system 20 is configured to provide maxillo-mandibular fixation (MMF) for assisting the repairing of an injury to the maxillo-mandibular region. For instance, when a jaw bone, such as a mandible 24 and/or maxilla 26, is fractured at a fracture location 37, it is desirable to stabilize the broken bone segments by fixing or stabilizing the maxilla and the mandible relative to each other. The fixation system 20 includes a pair of fixation devices 22 and 22', including bone fixation bodies 29 and 29', one or more fasteners 35 that attach each fixation body 29 and 29' to underlying bone, and one or more securement devices 23 that connect, or secure the fixation devices 22 and 22' to each other. The fasteners 35 can include bone screws or any other type of fastener suitable for attaching the fixation bodies 29 and 29' to underlying bone. Thus, the fixation devices 22 and 22' can be secured to the mandible 24 and the maxilla 26, respectively, of a patient. The suitable securement device 23 can secure the fixation bodies 29 and 29' to each other, thereby fixing the mandible 24 and the maxilla 26 with respect to relative movement.

Specifically, each fixation body 29 and 29' includes a respective plurality of flexible links 31 and 31' extending between a respective plurality of longitudinally spaced interfaces 33 and 33'. The pluralities of flexible links 31 and 31' extend upwardly and downwardly in an alternating pattern between the interfaces 33 and 33', thereby defining respective pluralities of valleys 30 and 30' and crests 32 and 32' between opposed ends of the fixation bodies 29 and 29'. The interfaces 33 and 33' defined at respective valleys 30 and 30' and crests 32 and 32' can be configured as securement or attachment locations. In the illustrated configuration, the interfaces 33 and 33' at the valleys 30 and 30' are configured as attachment locations having apertures 34 and 34', respectively. The apertures 34 and 34' can be configured to receive the fasteners 35. For example, the apertures 34 and 34' of the illustrated configuration are threaded so as to provide bone fixation holes such as screw holes that receive fasteners 35 in the form of bone screws. Accordingly, the valleys 30 and 30' are configured as attachment locations that can be attached to underlying bone, for instance via the bone screws. The interfaces 33 and 33' at the crests 32 and 32' are configured as connection, or securement locations which can be secured to each other to in turn secure the fixation devices 22 and 22' with respect to each other. In the illustrated configuration, the interfaces 33 and 33' at the crests 32 and 32' are defined as securement locations having tangs 36 and 36' that extend outwardly from the crests 32 and 32' in a direction generally towards and in between the immediately adjacent valleys 30 and 30', respectively. The tangs 36 and 36' can be configured to receive a securement device, for instance the securement device 23, so as to secure the tangs 36 and 36' to each other. The securement device 23 can be provided as a suitable wire, elastic band, or any other alternative securement apparatus as desired.

The mandibular and maxillo fixation devices 22 and 22' can be identically or substantially identically constructed from a bone fixation device 40 (see FIG. 2A), and oriented as desired when implanted into the mandible 24 and maxilla 26 of a patient to provide the fixation devices 22 and 22'. Thus, the vertical orientations of the fixation devices 22 and 22' are inverted with respect to each other in the illustrated configuration. In particular, the mandibular fixation device 22 is oriented such that the plurality of crests 32 are positioned above the plurality of valleys 30, and the maxillo fixation device 22' is oriented such that the plurality of crests 32' is positioned below the plurality of valleys 30'. The maxillo-mandibular fixation system 20 will now be described with reference to the bone fixation device 40 as illustrated in FIG. 2A.

The bone fixation device 40 is illustrated as oriented in a vertical plane defined by a longitudinal direction "L" and transverse direction "T" that is perpendicular to the longitudinal direction, and has a thickness in a lateral direction "A" that is perpendicular to the longitudinal and transverse directions L and T, respectively. The bone fixation device 40 is elongate along the longitudinal direction L before the fixation device 40 is curved, bent, or otherwise configured to align with, for instance, the mandible or maxilla prior to implantation. Thus, while the description of the bone fixation device 40 is made with reference to the illustrated configuration of the fixation device 40, the description applies equally to orientations achieved when the fixation device 40 is configured for implantation, for instance, in the maxilla or mandible of a patient.

Unless otherwise specified herein, the terms "lateral," "longitudinal," and "transverse" are used to describe the orthogonal directional components of the bone fixation device 40 and its components as illustrated in FIG. 2A. The terms "inner," "outer," and derivatives thereof with respect to a specified directional component are used herein with respect to a given apparatus to refer to directions along the directional component toward and away from the center of the apparatus, respectively.

It should be appreciated that while the longitudinal and transverse directions are illustrated as extending along a vertical plane, and that the lateral direction is illustrated as extending along a horizontal plane, that the planes that encompass the various directions may differ during use, depending, for instance, on the desired orientation of the bone fixation device 40 when implanted in a patient. Accordingly, while certain directional terms are used herein to describe the bone fixation device 40 as illustrated merely for the purposes of clarity and convenience, it should appreciated that these orientations may change during use.

Therefore, while the bone fixation device 40 is described with respect to an orientation such that its base (i.e., its valleys) is disposed below its crest (i.e., its crests), it can be subsequently oriented as desired (for instance with the base disposed above the crest when providing the maxillo fixation device 22') when implanted in the patient. It should thus be understood that while the bone fixation device 40 is described in its illustrated orientation with reference to implantation in the mandible 24, it can alternatively be implanted in the maxilla 26 or any other desired bone structures that are to be fixed relative to each other.

With continuing reference to FIG. 2A, the bone fixation device 40 includes a flexible bone fixation body 42, which can also be referred to as a fixation plate or a fixation body, and a plurality of fasteners 44 configured to attach the fixation body 42 to underlying bone. The fixation body 42 is illustrated as defining opposed first and second longitudinally outer ends 43 and 45, respectively, and opposed inner and outer lateral surfaces 57 and 59. The inner surface 57 faces the gum surrounding the bone structure to which the fixation body 42 is attached, and thus also faces the bone structure, and the outer surface 59 faces a direction opposite the inner surface 57. The fixation body 42 includes a plurality of sequential links 46A-E that can be integrally connected as illustrated, or can alternatively be discreetly attached to each other. The links 46A and 46E define outer links, while the links 46B-D define inner links disposed between the outer links 46A and 46E. In one embodiment, the fixation body 42 is formed by wire electrical discharge machining (wire EDM or waterjet machining), though the body can be formed from any alternative fabrication process. The fixation bodies 42 and 42' (see FIGS. 8-9) can be constructed from any suitable biocompatible material including but not limited to commercially pure titanium, titanium alloy such as TAN, stainless steel, reinforced plastics, polymers such as polyether ether ketone (PEEK) or PE, and the like.

As illustrated, the fixation body 42 includes five links 46A-E, though any number of links can be used such that reliable fixation can be achieved to a patient's mandible or maxilla, such as three links, four links, or five links. Referring to FIG. 2B, the links 46A-E have a rectangular cross-section that is elongate in the vertical plane defined by the transverse T and longitudinal L directions. It should be appreciated that the links 46A can define any cross-sectional shape as desired, such as square, or any suitable alternative shape. Specifically, the links 46A-E include opposed elongate edges 47 and minor edges 49. The elongate edges 47 can have any length as desired, such as about 1 mm while the minor edges 49 can have any length as desired, such as about 0.6 mm. The links 46A-E can define a lateral thickness as desired, such as approximately 0.6 mm in accordance with one embodiment. Of course, it may be desirable to eliminate sharp corners or edges that could cause injury to surrounding tissue when implanted in a patient. The size and shape of the links 46 impart flexibility to the fixation body 42, thereby allowing the fixation body 42 to assume multiple sizes, and also allowing for variable positioning of the fixation device 40 when implanted in the patient. In this regard, it should be appreciated that the links 46A-E can alternatively define any suitable alternative geometric size and shape as desired. One or more of the links 46A-E can be similarly or identically or substantially identically constructed, and will now be described with reference to the link 46B.

In particular, referring again to FIG. 2A, the link 46B includes a pair of opposed first and second side members 48 and 50. Each side member defines respective longitudinally inwardly curved upper ends 52 and 54 and opposed longitudinally outwardly curved lower ends 56 and 58. The upper ends 52 and 54 of the side members 48 and 50 of the link 46B are joined at a first interface 53, so as to form a crest 51 of the fixation body 42. The crest 51 is continuously curved about a laterally extending axis, such that the crest 51 presents a convex surface with respect to a downwardly directed view of the top of the fixation body 42. Of course, it should be appreciated that the crest 51 could assume any alternative shape as defined by the upper ends 52 and 54 of the side members 48 and 50, or as defined by a separate structure that joins the upper ends 52 and 54, either directly or indirectly. For instance, a portion up to all of at least one or more up to all of the crests 51 can be flat.

The side members 48 and 50 are longitudinally spaced from each other, and extend linearly so as to flare longitudinally outward from each other along a downward direction from their respective upper ends 52 and 54 to their lower ends 56 and 58 in the illustrated embodiment. Thus, the first side member 48 flares longitudinally outward toward the first outer end 43 of the fixation body 42 in a downward direction along the side member 48. Likewise, the second side member 50 flares longitudinally outward toward the second outer end 45 of the body in a downward direction along the side member 50. In the illustrated embodiment, the side members 48 and 50 flare equally outward with respect to a transverse midline TM of the link 46B at a desired angle θ anywhere between 0° and 90°, for instance between 0° and 45°, such as approximately 14°.

The lower end 56 of the first side member 48 of the link 46B is connected to the lower end 58 of the side member 50 of the adjacent link 46A at a second interface 53 to form a valley 60 of the fixation body 42, and the lower end 58 of the side member 50 of the link 46B is connected to the lower end 56 of the side member 48 of the adjacent link 46C at a third interface 53 to likewise form another valley 60 of the fixation body 42. The valleys 60 are continuously curved about a laterally extending axis, such that the valley presents a convex surface with respect to an upwardly directed view of the bottom of the fixation body 42. Of course, it should be appreciated that the valleys could assume any alternative shape as defined by the lower ends 56 and 58 of the side members 48 and 50, or as defined by a separate structure that joins the lower ends 56 and 58 of adjacent links, either directly or indirectly. For instance, a portion up to all of at least one or more up to all of the valleys 60 can be flat. The side members 48 and 50 of each link are integrally connected to the complementary side members of the adjacent links at the interfaces 53, though they could alternatively be discreetly attached to each other at the interfaces 53. Furthermore, the side members 48 and 50 can assume any size and shape as desired that connects the crest 51 to the valleys 60, either directly or indirectly.

The fixation body 42 can define any desired longitudinal distance, or width W between adjacent valleys 60, and therefore between adjacent crests 51, such as approximately 20 mm, and any desired transverse height H between the lower edge of the valley 60 and the upper edge of the crest 51 along the transverse direction T, such as approximately 17.6 mm. The fixation body 42 can be configured such that a spatial relationship is defined between the respective crests 51 and/or valleys 60. For example, the spatial relationship can be defined such that the width W between each of the crests 51 and the width W between each of the valleys 60 is uniform throughout the fixation body 42, as illustrated. Alternatively, the spatial relationship can be defined with two or more crests 51 separated by different widths W, two or more valleys 60 separated by different widths W, or any combination thereof. Of course spatial relationships with respect to the height H between the crests 51 and the valleys 60 can also be defined. The side members 48 and 50 can be flat, curved, or otherwise shaped as desired between the interconnected crests 51 and valleys 60. Further, it should be appreciated that the height H of each of the links can be the same each other. Alternatively, the height H of one or more of the links can be different than one or more up to all of the links. Further, the width W can be constant along the fixation body 42 when the fixation body 42 is in a neutral configuration. Alternatively, the width W can vary along the fixation body 42 when the fixation body 42 is in the neutral configuration.

It should be appreciated that although the links 46A-E of the illustrated configuration are all the same size and shape, that one or more, up to all of the links 46A-E of the fixation body 42 can have different sizes and/or shapes, for example having different widths W, heights H, or any combination thereof. It should further be appreciated that the links 46A-E need not all have the same cross-section, as defined between the elongate edges 47 and the minor edges 49. For example, it may be desirable to configure one or more of the links 46A-E with different lateral thicknesses, for instance to control the deformation characteristics of particular links when the fixation body 42 is flexed inwardly or outwardly in the longitudinal direction L, or otherwise shaped prior to implantation in a patient, as described in more detail below. Furthermore, the cross section within an individual link can be varied along one or more portions between its respective adjacent valleys 60.

It should be appreciated that the links 46A-E define an undulating fixation body 42 shaped in a wave-form having wave segments that are proportional in number to the number of links 46. While five links 46A-E are illustrated, the fixation body 42 can include any number of links 46A-E as desired. Each link 46A-E is illustrated as defining a crest 51 of the wavelike structure, and a portion of a valley 60 of one or more adjacent wavelike structures. It should also be appreciated that the longitudinal widths W and transverse heights H can vary between adjacent crests and valleys. For instance, one or more of the crests 51 can have a height H greater or lesser than that of one or both of the immediately adjacent crests.

The side member 48 of the outer link 46A disposed at the first end 43 of the fixation body 42 terminates at its lower end 56, while the side member 50 of the outer link 46E disposed at the second end 45 of the fixation body 42 terminates at its lower end 58. Alternatively, it should be appreciated that a half-link could be disposed at the opposed outer ends 43 and 45, such that each half-link would terminate at their respective upper ends 52 and 54, or at any alternative location along their lengths as desired. In the illustrated embodiment, the lower end 56 of the side member 48 of the outer link 46A and the lower end 58 of the side member 50 of the outer link 46E terminate at respective bone attachment locations 70, as will be described in more detail below.

The fixation body 42 includes a plurality of bone attachment locations 70 that facilitate attachment of the fixation body to the underlying bone. For instance, as described above, the fixation body 42 can be attached to an underlying mandible or maxilla, or any alternative bone structure, such that a bone fracture is disposed between the opposed outer ends 43 and 45 of the fixation body 42. Accordingly, in the instance of mandibular or maxillo fixation, when a pair of fixation bodies 42 are secured to each other in the manner described above with respect to FIG. 1, the broken bone segments are relatively immobilized to facilitate healing.

In the illustrated embodiment, the bone attachment locations 70 are provided as screw holes 72 extending laterally through the fixation body 42 at the respective valleys 60, though one or more alternatively configured attachment locations can be provided in any suitable manner so as to facilitate attachment of the fixation body 42 to underlying bone. The screw holes 72 can be sized to threadedly receive corresponding fasteners 44, provided in one embodiment as bone screws 74. Specifically, referring to FIG. 6, the fixation body 42 includes a beveled inner surface 76 that defines each screw hole 72, and is sized and shaped to receive a correspondingly beveled outer surface 78 of a screw head 80. The beveled surface 76 is positioned such that the screw head 80 does not protrude outwardly from the fixation body 42 when fully seated in the screw hole 72. As illustrated, the screw head 80 is flush with the outer surface 59 of the fixation body 42, though the screw head 80 could alternatively be inwardly recessed or slightly outwardly protruding with respect to the outer surface 59 of the fixation body 42.

Of course, the screw hole 72 could assume one of numerous configurations, such that the inner surface 76 can be beveled straight, or rounded at any desired radius, for instance approximately 3.6 mm. Alternatively still, the inner surface 76 need not be beveled, and can extend laterally in a direction parallel to the outer surface of the screw head 80. As another example, while the inner surface 76 is illustrated as smooth and flat, the inner surface 76 could alternatively be threaded to threadedly engage corresponding threads of the screw head 80, such that the screw 74 would be self-locking within the screw hole 72. It should also be appreciated that the bone screws 74 can be self-drilling, or could alternatively be insertable into a pre-drilled hole as appreciated by one having ordinary skill in the art. The fixation device 40 can further include a collar that surrounds the screw hole 72 at the inner surface 57 of the fixation body 42, such that the collar would be disposed between the fixation body 42 and the underlying bone structure. The collar would thus provide a stand-off that spaces the fixation body 42 from the patient's gum when the bone screws 74 are fully inserted into the underlying bone.

As described above, the links 46A-E are constructed so as to impart a flexibility to the fixation body 42. Specifically, the fixation body can bend about a transverse axis to conform generally with dental arches of patients of different sizes and shapes, thereby allowing the bone screws 74 to be inserted into the screw holes 72 and screwed into an underlying mandible or maxilla, as illustrated in FIG. 1. Furthermore, referring to FIGS. 3A-C, the links 46A-E can allow the fixation body 42 to flex longitudinally.

For instance, FIGS. 2A and 3A illustrate the fixation body 42 in an initial relaxed, or neutral configuration, whereby the fixation body is in its as-manufactured configuration prior to inward or outward flexing along the longitudinal direction L. In the neutral configuration, the fixation body 42 can define any longitudinal distance LI as desired between the opposed longitudinally outermost edges, such as approximately 100 mm.

However, as shown in FIG. 3B, a longitudinally inwardly directed force can be applied to one or more, including all, of the links 46, thereby compressing the crests 51 and/or valleys 60 and achieving a reduced longitudinal length LR of the fixation body 42 to a distance less than the initial distance LI, as desired. The fixation body 42 can be configured such that when the length of the fixation body 42 is adjusted by longitudinal compression, the longitudinal distance, or spacing between the crests 51 and/or valleys 60 (i.e., the width W (FIG. 2A) between adjacent crests 51 and/or valleys 60) in the compressed configuration of the fixation body 42 is preserved with respect to the relaxed or neutral configuration of the fixation body 42. In other words the spacing, or width W between adjacent crests 51 and/or valleys 60 of the fixation body 42 will be smaller after the longitudinal compression, but the crests 51 and/or valleys 60 can maintain their spatial relationship; for instance the crests 51 can still be spaced apart equally as they were in the neutral configuration, and the and valleys 60 can also be spaced apart equally as they were in the neutral configuration.

Additionally, as shown in FIG. 3C, a longitudinally outwardly directed force can be applied to one or more, up to all, of the links 46, thereby extending the crests 51 and/or valleys 60 and achieving an extended, or expanded longitudinal length LE of the fixation body 42 to a distance greater than the initial distance LI, as desired. The fixation body 42 can be configured such that when the length of the fixation body 42 is adjusted by longitudinal expansion, the longitudinal distance, or spacing between the crests 51 and/or valleys 60 (i.e., the width W between adjacent crests 51 and/or valleys 60) in the expanded configuration of the fixation body 42 is preserved with respect to the neutral configuration of the fixation body 42. In other words the spacing, or width W between adjacent crests 51 and/or valleys 60 of the fixation body 42 will be greater after the longitudinal expansion, but the crests 51 and/or valleys 60 can maintain their spatial relationship; for instance the crests 51 can still be spaced apart equally as they were in the neutral configuration, and the and valleys 60 can also be spaced apart equally as they were in the neutral configuration. It should be appreciated that the fixation body 42 can be configured such that the transverse height H between the crests 51 and/or valleys 60 after the fixation body 42 is compressed and/or expanded is similarly preserved with respect to the neutral configuration of the fixation body 42.

It should therefore be appreciated that the bone attachment locations 70 can remain aligned with the underlying bone even as the fixation body 42 is flexed longitudinally inward and/or outward. Furthermore, the bone attachment locations 70 can be aligned or substantially aligned with each other along a longitudinal axis LA even as the fixation body 42 is flexed longitudinally inward and outward. In one embodiment, the fixation body 42 can stretch or compress lengthwise longitudinally an amount between 5% and 50% with respect to its length in the relaxed position, for instance between 10% and 40%, and more particularly between 20% and 30%, and more particularly still about 23%. The fixation body 42 can further stretch or compress height-wise transversely by any suitable percentage with respect to its height in the relaxed position, such as between 1% and 25%, for instance between 5% and 15%, and more particularly about 11%. It should be appreciated that when the body 42 is stretched longitudinally, the body 42 tends to shrink or compress transversely, and vice versa. Furthermore, when the body 42 is compressed longitudinally, the body 42 tends to stretch transversely, and vice versa.

Thus, the configuration of the fixation body 42 can be adjusted in situ while implanting the fixation device 40 in the patient. For instance, the fixation body 42 can be sized and configured as desired based on the size of the underlying bone segments to be fixed. Additionally, the fixation body 42 can be sized and configured to place the securement locations in a desired position prior to fastening the fixation body 42 to underlying bone. Furthermore, the side members 48 and 50 allow the fixation body 42 to be bent or otherwise configured in the vertical plane as well, for instance, when aligning the fixation body 42 with underlying bone. While the fixation body 42 is flexible, the continuity between adjacent links 46 provides sufficient stiffness when the fixation device 40 is affixed to underlying bone and attached to a complementary fixation device in a fixation system.

It should be appreciated that the fixation body 42 can be constructed so as to allow the fixation body 42 to extend and/or compress as desired. In this regard, the fixation body 42 includes at least two side members that are longitudinally spaced from each other by an interface 53 that can expand and compress in response to expansive and compressive forces. As illustrated, the interfaces 53 are curved surfaces (e.g., the crests 51 and valleys 60) whose curvature can be increased and reduced through flexing, though the interfaces 53 can alternatively include angled connections between the side members 48 and 50. The compressive and expansive deformation of the fixation body 42 can be plastic, or can alternatively be elastic such that the deformed shape is retained when the fixation body 42 is attached to the underlying bone at the attachment locations 70. Of course, the height of the fixation body 42 may increase slightly when the fixation body 42 is compressed, and may decrease slightly when the fixation body 42 is extended.

Figure 4:
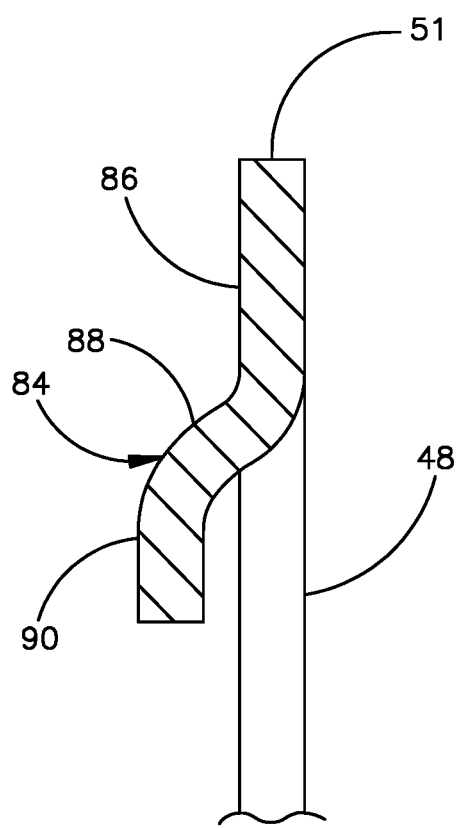
FIG. 4 is a sectional elevation view of the fixation device illustrated in FIG. 2A, taken along line 4-4.

Referring again to FIG. 2A and also to FIG. 4, the fixation device 42 further includes a plurality of connection, or securement locations 82 configured to facilitate connecting, or securing together a pair of fixation devices 40 that are inversely oriented, for instance when implanted in a mandible and maxilla, respectively. In the illustrated configuration, the securement locations 82 are disposed at the longitudinal midpoint, or apex of the crest 51 of each of the links 46A-E. However, it should be appreciated that alternatively, the securement locations 82 can be disposed anywhere on the fixation body 42 as desired. It should be appreciated that each crest 51 can support a respective securement location 82. Alternatively, one or more of the crests 51 can be devoid of a securement location, such that one or more crests 51 can be disposed between adjacent securement locations 82. Alternatively still, one or more up to all of the links can include one or more securement locations 82 as desired. Alternatively or additionally, one or more up to all of the links can include one or more attachment locations 70 as desired. The securement locations 82 can be configured to allow a securement member, such as the securement device 23 described above with respect to FIG. 1, to connect a pair of fixation bodies 42 to each other so as to restrict relative movement of the bone underlying the connected fixation bodies 42.

The securement locations 82 are provided in the illustrated embodiment as tangs 84 extending down from the apex of each crest 51 of the fixation body 42. Otherwise stated, the tangs 84 extend in a generally transverse direction from the crest 51 toward a longitudinal axis LA that extends through the screw holes 72. One or more, up to all, of the tangs 84 can also include longitudinally or laterally extending segments as well, if desired. For instance, in the illustrated embodiment, each of the tangs 84 includes a first segment 86 that extends downward along the transverse direction T from the transverse inner edge of the apex of the crest 51. A second, or spacer, segment 88 extends in the downward direction and outward along the lateral direction A from the lower end of the first segment 86. A third segment 90 extends down in the transverse direction T from the lower end of the spacer segment 88.

Thus, a securement device, such as the securement device 23 described above, can engage the lower surface of the spacer segment 88 and laterally inner surface of the third segment 90 when fixing or stabilizing a pair of mandibular and maxillo fixation bodies 42 to each other. Alternatively or additionally, the securement device 23 can engage the laterally inner surface of the first segment 86 and the laterally outer surface of the crest 51. For instance, a wire can be wrapped around the tang 84 and/or link 46. Alternatively or additionally, an elastic band can be seated at one end between the tang 84 and the crest 51. Because securement devices 23 can be attached at multiple locations along the length of the fixation body 42, the resulting forces associated with coupling the securement devices 23 to a complementary fixation body 42 distributes the resulting forces substantially equally across the length of the fixation body 42.

Figure 5:
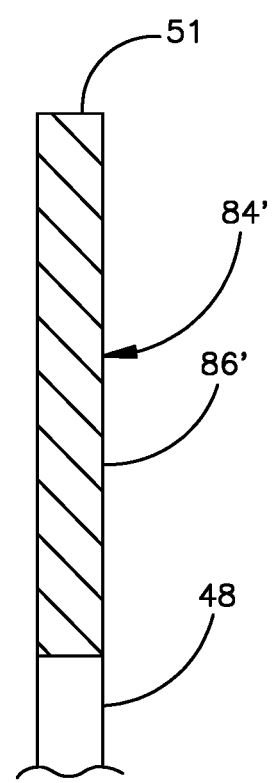
FIG. 5 is a sectional elevation view of the fixation device similar to FIG. 4, but illustrated in accordance with an alternative embodiment.

Alternatively, referring now to FIG. 5, one or more, up to all, of the tangs 84' can include a single segment 86' constructed similarly with respect to the segment 86, thus extending vertically down from the crest 51 in the manner describe above. Thus the tang 84' does not include any lateral or longitudinal directional components. The securement device 23 can be wrapped around the segment 86' in the case of a wire, for instance, or can be seated between the segment 86' and the crest 51 in the case of an elastic band. Alternatively still, it should be appreciated that the securement locations 82 can include the crest 51 itself, without any tangs 84 or other additional structure. For instance, a plurality of elastic bands could be slid along the wavelike form of the fixation body 42 to locations at respective crests 51 prior to implantation of the fixation body 42 into underlying bone. Alternatively, a wire could be wrapped around the crests 51 of opposed fixation bodies 51 prior to or after implantation of the fixation bodies 42. Alternatively still, the securement location 82 could be provided as an aperture extending laterally through the links 46A-E, for instance at their crests 51.

The fixation device 40 was illustrated and described above in accordance with one embodiment, it being appreciated that numerous alternative embodiments are contemplated.

For instance, referring to now FIG. 7, the fixation body can include auxiliary links, and can alternatively or additionally include securement locations that are positioned differently than the securement locations 82 described above. As illustrated in FIG. 7, the fixation body 42 can include auxiliary links 92 connected between adjacent links 46. The auxiliary links 92 can extend between the first and second side members 48 and 50 of adjacent links 46 at any respective desired locations along the first and second side members 48 and 50, respectively. For instance, in the illustrated embodiment, the auxiliary links 92 extend between the first and second side members 48 and 50 at locations proximate to, or at, the respective upper ends 52 and 54 of the first and second side members 48 and 50. The auxiliary links 92 are illustrated as extending transversely upward and inward from the side members 48 and 50 toward an auxiliary crest 94 that is shaped substantially as described above with respect to the crests 51. Thus, the auxiliary crest 94 presents a convex surface with respect to a downwardly directed view of the top of the fixation body 42, though the auxiliary crest 94 could also assume any alternative shape as desired. The auxiliary crests 94 allow the auxiliary links 92 to expand and contract as described above with respect to FIGS. 3A-C, though the auxiliary links 92 can be configured to add an amount of stiffness to the fixation body 42 with respect to the fixation body 42 as illustrated in FIG. 2A without the auxiliary links 92. The auxiliary crests 94 can be positioned longitudinally midway between the crests 51 of the links 46A-E, which can be referred to as "primary" links 46A-E when the fixation body 42 includes the auxiliary links 92.

As illustrated in FIG. 7, one or more, up to all of the auxiliary links 92 can be configured as auxiliary securement locations 96, constructed differently or as described above with respect to the securement locations 82. The auxiliary securement locations 96 can be provided anywhere along the auxiliary links 92, such as at the apexes of the auxiliary crests 94. Thus, for instance, the auxiliary securement locations 96 can be configured to allow a securement member, such as the securement device 23 described above with respect to FIG. 1, to connect a pair of fixation bodies 42 to each other so as to restrict relative movement of the bone underlying the connected fixation bodies 42. In the illustrated embodiment, the auxiliary securement locations 96 are provided as tangs 98 that extend from the auxiliary crests 94 as described above with respect to tangs 84 and 84' extending from respective crests 51. It should be appreciated that the auxiliary securement locations 96 can be provided in addition to the securement locations 82, as an alternative to the securement locations 82, or that any combination of the securement locations 82 and/or the auxiliary securement locations 96 can be provided as desired.

Referring now to FIG. 8, a portion of a fixation body 42' is illustrated as including a plurality of links 46' that are shaped differently with respect to the straight side members 48 and 50 of the links 46A-E illustrated in FIG. 2A. For instance, as illustrated, the side members 48' and 50' of a given link 46' can be longitudinally inwardly curved toward each other from their respective lower end 56' and 58' near their respective valleys 60' in a transverse upward direction along the side members 48' and 50' toward the crest 51', then longitudinally curved outwardly away from each other in a continuing transverse upward direction, and finally longitudinally curved inwardly toward each other again at the respective upper ends 52' and 54' of the side members 48' and 50' near the crest 51'. It should be appreciated that the illustrated curvature of the side members 48' and 50' is an example of alternative curvature for the links 46', and that the side members 48' and 50' can be configured with any other alternative curvature as desired. It should further be appreciated that the fixation body 42 of a fixation device 40 can be configured entirely of links 46', thereby providing a fixation body 42', or can be configured with any combination of the links 46' and the links 46 as described above with reference to FIGS. 2A-B, as desired. The curved side members 48' and 50' can be configured to allow the fixation body 42' to flex in the transverse direction. Accordingly, when a pair of fixation devices 40 having fixation bodies 42' are secured to each other as illustrated in FIG. 1, the fixation devices 40 can flex toward each other in response to the forces applied by the securement device 23. It should be appreciated that the fixation body 42' can further include auxiliary links and/or auxiliary securement locations as described above with reference to FIG. 7.

Furthermore, as described above, the lower end 56 of the side member 48 of the outer link 46A and the lower end 58 of the side member 50 of the outer link 46E terminate at respective bone attachment locations 70, as illustrated in FIG. 2A. Accordingly, as illustrated in FIG. 2A, the bone fixation device 40 can terminate at outermost bone attachment locations 70. Alternatively, as illustrated in FIG. 9, in which the bone fixation device 40' includes three links 46A'-C', the outermost links 46A' and 46C' are attached to outermost securement locations 82' via arms 50" and 48", respectively. The arms 50" and 48" extend longitudinally outwardly from the ends 43' and 45' of the fixation body 42', between lower arm ends 56" and 58" and upper arm ends 52" and 54", respectively. However, it should be appreciated that the bone fixation device 40' as illustrated in FIG. 9 could be constructed as described above with reference to FIG. 2A, or any alternative embodiments described herein. Thus, the outermost securement locations 82' are disposed longitudinally outward with respect to the outermost bone attachment locations 70'. As illustrated, the fixation body 42' can include four bone attachment locations 70' as illustrated, or any alternative number of bone attachment locations 70' as desired. The outermost securement locations 82' can be disposed above, below, or at a transverse height substantially equal to that of the other securement locations 82' of the bone fixation device 40'. In the illustrated embodiment, the outermost securement locations 82' are disposed at a transverse height below that of the other securement locations 82' of the bone fixation device 40'.

The outermost securement locations 82' can be provided as hooks 83' extending in the longitudinal-transverse plane, or any alternative plane as desired, for example from the upper arm ends 52" and 54" of the arms 50" and 48", respectively. Thus, a securement device, such as device 23 described above, can engage the hooks 83' of opposed fixation bodies 42' when fixing or securing a pair of mandibular and maxillo fixation bodies 42' to each other. In this regard, it should be appreciated that any of the securement locations described herein could comprise hooks or any alternative structure suitable for connecting, or securing a pair of fixation devices as described above.

Figure 10:
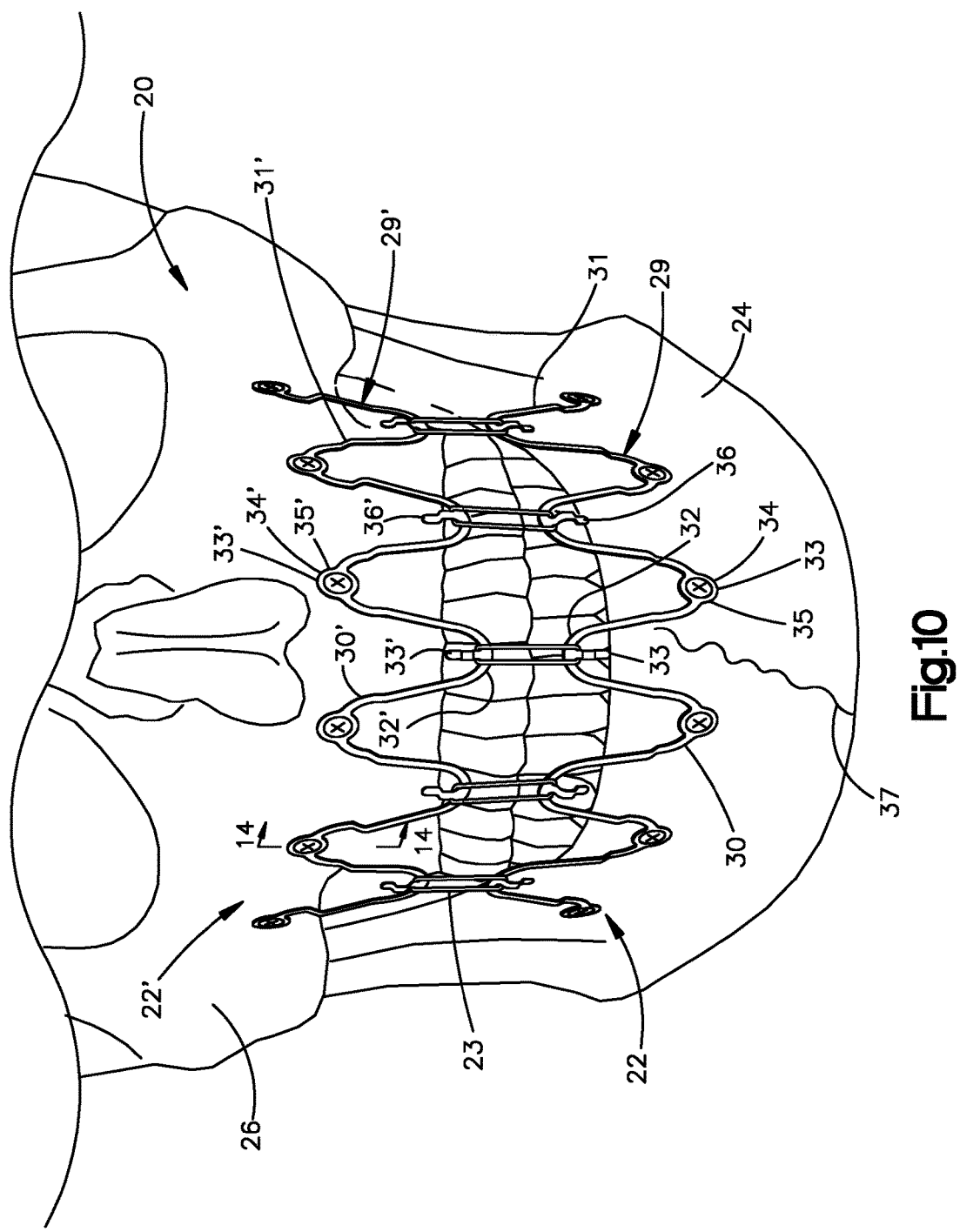
FIG. 10 is a perspective view of the maxillo-mandibular fixation system as illustrated in FIG. 1, but wherein the fixation devices define an offset in accordance with another embodiment.

Referring now to FIG. 10, the bone fixation system 20 can include the first and second bone fixation devices 22 and 22' that can be identically or substantially identically constructed from the bone fixation device 40 (see FIG. 12) substantially as described above. Additionally, the first and second bone fixation bodies 22 and 22' can be configured such that the valleys 30 are offset with respect to the crests 32, and the valleys 30' are offset from the crests 32'. As a result, when the first bone fixation body 22 is attached to the mandible 24, the valleys 30 are disposed closer to the mandible 24 than a distance that the crests 32 are spaced from the mandible. Similarly, the valleys 30' are disposed closer to the maxilla 26 than a distance that the crests 32' are spaced from the maxilla.

Referring now also to FIGS. 11-14, the bone fixation device 40 includes the flexible bone fixation body 42 and the plurality of fasteners 44 (see also FIG. 2A) configured to attach the fixation body 42 to underlying bone, as described above. The bone fixation body 42 includes a plurality of links 46 that are spaced from each other along a first direction. It is appreciated that when the bone fixation body 42 is in a first configuration, such as a neutral or relaxed configuration, the first direction can be the straight longitudinal direction L. When the bone fixation body 42 is in the flexed configuration (see FIG. 10), the first direction can be a curved direction 40 that fits the bone fixation body 42 to the underlying bone.

The links 46, in combination, define the plurality of securement locations 82, the plurality of attachment locations 70 that are offset from the securement locations 82 along a second direction substantially perpendicular to the first direction. For instance, when the bone fixation body 42 is in the first configuration, the second direction can be defined by the transverse direction T. The bone fixation body 42 can further include a plurality of side members 48 and 50 that extend from respective ones of the securement locations 82 to respective adjacent ones of the attachment locations 70. It is appreciated that the side members 38 and 50, the securement locations 82, and the attachment locations 70 of the fixation body 42 can all be monolithic with each other, thereby defining a one-piece structure. As described above, the securement locations 82 and the attachment locations 70 can be alternatingly arranged along the fixation body 42.

The side members 48 and 50 can each define a respective offset region 71 that offsets the securement locations 82 from the attachment locations 70 along a third direction that is substantially perpendicular to each of the first and second directions. When the bone fixation body 42 is in the first configuration, the third direction can be defined by the lateral direction A. In one example the side members 48 and 50 can define crests 51 that each supports a respective one of the securement locations 82, as described above. The side members 48 and 50 can further define valleys 60 that each defines a respective one of the attachment locations 70 as described above. Further, the offset region 71 can cause the valleys 60 to be offset from the crests 51 along the third direction. It is appreciated that the first, second, and third directions may be substantially perpendicular to each other. For instance, when the fixation body 42 is in a bent or flexed configuration, the first, second, and third directions may not be precisely perpendicular to each other.

Further, as described above, the fasteners 44 are configured to be driven or embedded into underlying bone at respective ones of the attachment locations 70, thereby attaching the fixation body 42 to the underlying bone. The securement locations 82 are configured to engage with respective ones of the securement devices 23 so as to secure the fixation device 42 to complementary securement members of an identical second fixation device. 40. For instance, the first and second fixation devices 40 can be arranged as illustrated in FIG. 10 with respect to the first and second fixation devices 22 and 22'.

Because the securement locations 82 are outwardly offset from the attachment locations 70 along the third direction, when the fasteners 44 are embedded into the underlying bone 24 at the respective ones of the attachment locations 70 (see FIG. 14), the attachment locations 70 are disposed closer to the underlying bone along the third direction than a distance that the securement locations 82 are spaced from the underlying bone along the third direction. Accordingly, the securement devices 23 and securement locations 82 can be spaced from soft tissue that surrounds the underlying bone.

As described above, for instance with respect to FIGS. 1, 2, and 12, the bone fixation body 42 can include a plurality of securement locations 82 and a plurality of attachment locations 70. For instance, the securement locations 82 can be disposed at respective ones of the crests 51, and the attachment locations 70 can be disposed at respective ones of the valleys 60. It is recognized, however, that the securement locations 82 and the attachment locations 70 can alternatively be located at any suitable location of the bone fixation body 42, and can be present in any arrangement as desired. For instance, the securement locations 82 and the attachment locations 70 can be alternatingly arranged along the longitudinal direction L. For instance, each crest 51 can support a respective one of the securement locations 82, and each valley 60 can support a respective one of the attachment locations 70. Alternatively, one or more of the crests 51 can be devoid of a securement location 82. Similarly, one or more of the valleys 60 can be device of an attachment location 70.

Figure 15A:
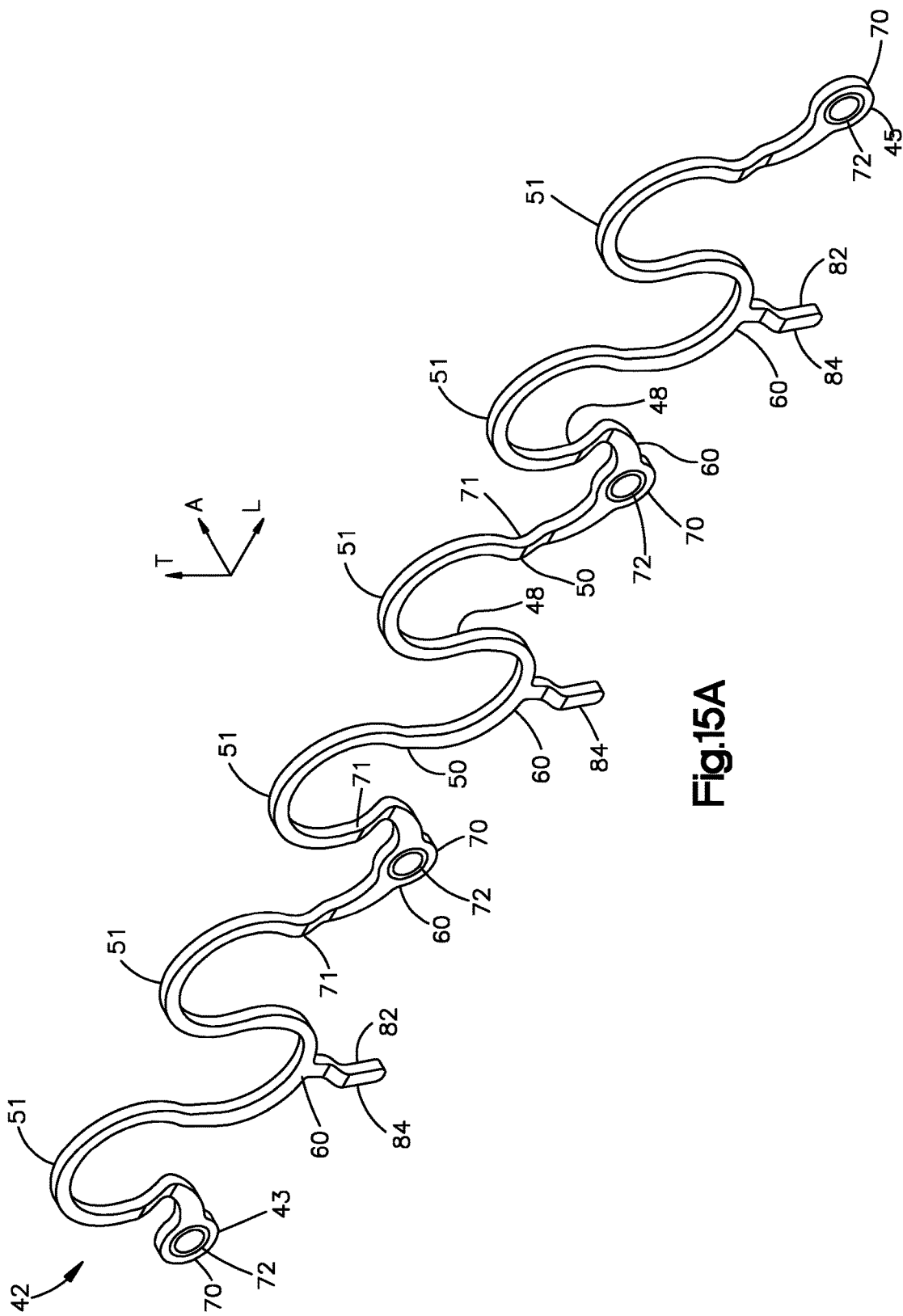
FIG. 15A is a perspective view of a bone fixation body similar to the bone fixation body illustrated in FIG. 12, but constructed in accordance with an alternative embodiment.

For instance, referring now to FIG. 15A, all of the crests 51 can be devoid of securement locations 82 and attachment locations 70. Rather, one or more of the valleys 60 can support the securement locations 82, and one or more of the valleys 60 can support the attachment locations 70 as described above. Thus, both the attachment locations 70 and the securement locations 82 can be supported at the valleys 60. Accordingly, at least some up to all of the attachment locations 70 and the securement locations 82 can be aligned with each other with respect to the longitudinal direction L. For instance, the attachment locations 70 and the securement locations 82 can be alternatingly arranged along the longitudinal direction L. It should be appreciated, however, that the attachment locations 70 and the securement locations 82 can be disposed in any suitable alternative arrangement as desired. The free ends of the tangs 84 of the securement locations 82 can extend out from the valleys 60 along a direction from the crests 51 toward the valleys 60 so as to facilitation attachment of the securement members 23 to the bone fixation body 42. Thus, the tangs 84 can extend out from the valleys 60 in a direction opposite the opposed bone fixation body 42. The bone fixation body 42 can further include a plurality of offset regions 71 between the valleys 60 that support the attachment locations 70 and the valleys 60 that support the securement locations 82. The offset regions 71 can cause the securement locations 82 to be spaced outward with respect to the attachment locations 70 along the lateral direction A as described above with respect to FIGS. 10-13. The offset regions 71 can be defined by the side walls 48 and 50 that extend from the valleys 60 that support the attachment locations 70, though it should be appreciated that the offset regions 71 can be defined by the side walls 48 and 50 that extend from the valleys 60 that support the securement locations 82.

Figure 15B:
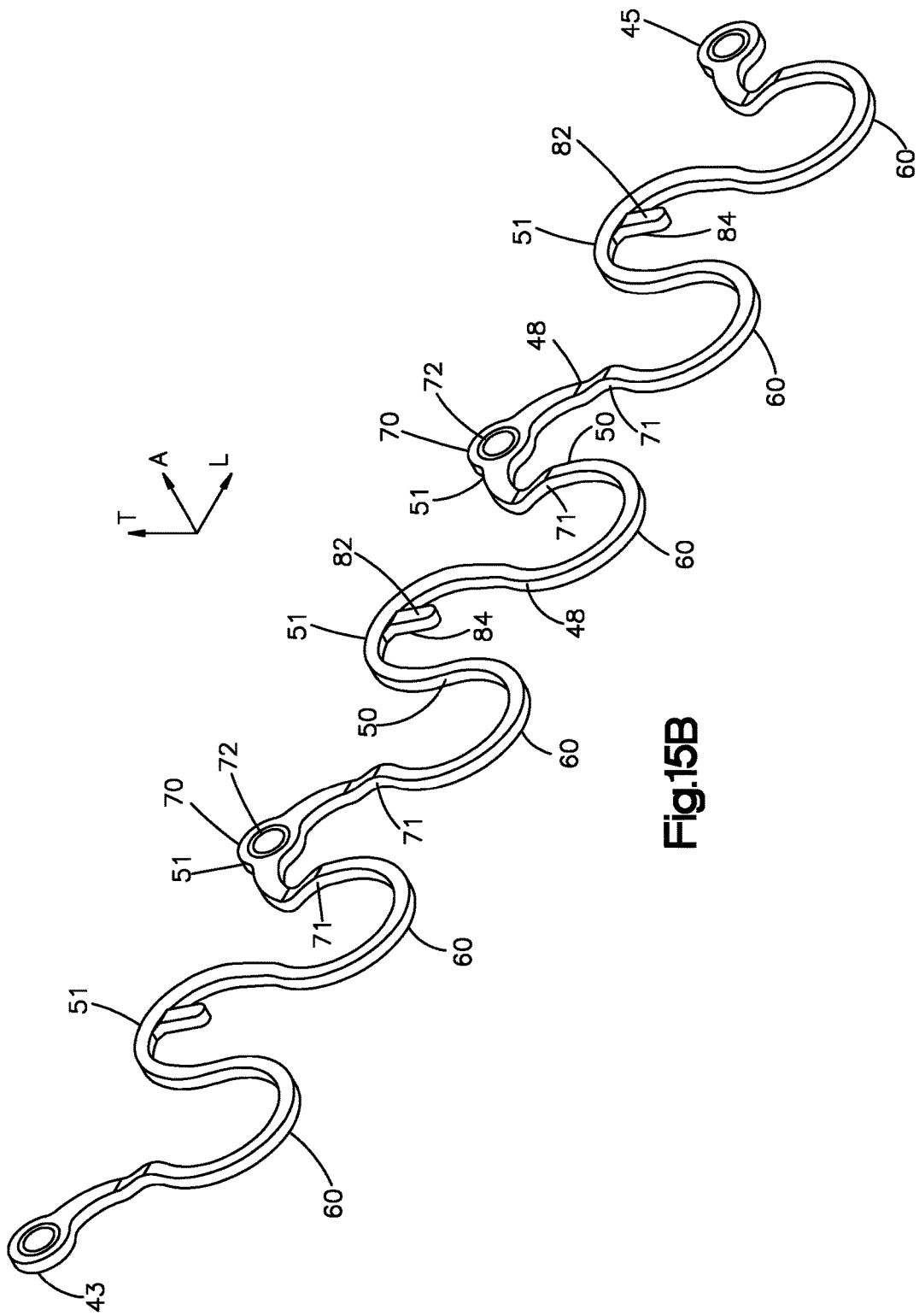
FIG. 15B is a perspective view of a bone fixation body similar to the bone fixation body illustrated in FIG. 15A, but constructed in accordance with an alternative embodiment.
Figure 20:
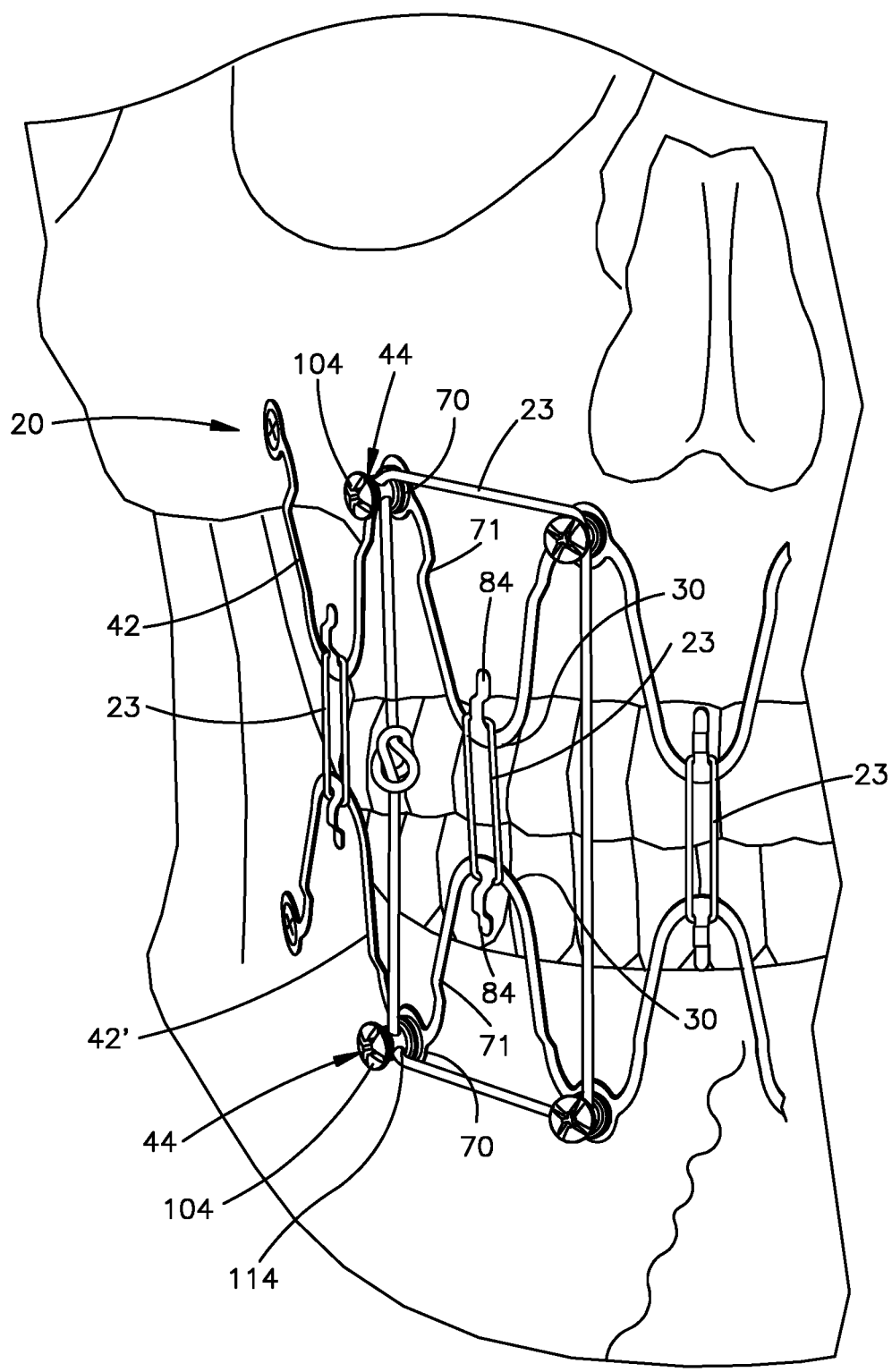
FIG. 20 is a perspective view of a portion of the maxillo-mandibular fixation system as illustrated in FIG. 10, but wherein the fasteners are constructed as illustrated in FIG. 19A.

Alternatively, as illustrated in FIG. 15B, all of the valleys 60 can be devoid of securement locations 82 and attachment locations 70. Rather, one or more of the of the crests 51 can support the securement locations 82, and one or more others of the crests 51 can support the attachment locations 70 as described above. Thus, both the attachment locations 70 and the securement locations 82 can be supported at the crests 51. Accordingly, at least some up to all of the attachment locations 70 and the securement locations 82 can be aligned with each other with respect to the longitudinal direction L. For instance, the attachment locations 70 and the securement locations 82 can be alternatingly arranged along the longitudinal direction L. It should be appreciated, however, that the attachment locations 70 and the securement locations 82 can be disposed in any suitable alternative arrangement as desired. The free ends of the tangs 84 of the securement locations 82 can extend out from the crests 51 along a direction from the crests 51 toward the valleys 60 so as to facilitation attachment of the securement members 23 to the bone fixation body 42. Thus, the tangs 84 can extend out from the valleys 60 in a direction opposite the opposed bone fixation body 42. The bone fixation body 42 can further include a plurality of offset regions 71 between the crests 51 that support the attachment locations 70 and the crests 51 that support the securement locations 82. The offset regions 71 can cause the securement locations 82 to be spaced outward with respect to the attachment locations 70 along the lateral direction A as described above with respect to FIGS. 10-13. The offset regions 71 can be defined by the side walls 48 and 50 that extend from the crests 51 that support the attachment locations 70, though it should be appreciated that the offset regions 71 can be defined by the side walls 48 and 50 that extend from the crests 51 that support the securement locations 82. It should be appreciated, of course that each of the crests 51 and valleys 60 can support both attachment locations 70 and securement locations 82 in any suitable arrangement as desired.

The bone attachment locations 70 can be configured as screw holes 72 that extend along the lateral direction A through the fixation body 42 at the respective valleys 60. The screw holes 72 can be sized to threadedly receive corresponding fasteners 44, provided in one embodiment as bone screws 74. The fixation body 42 can include a plurality of inner surfaces 76 that define respective ones of the screw holes 72. The inner surfaces 76 can be sized and shaped to receive the corresponding outer screw surface 78 of the screw head 80. For instance, the inner surfaces 76 and the outer screw surfaces 78 can be beveled or otherwise tapered or shaped as desired. In accordance with one embodiment the inner surfaces 76 are positioned such that the screw head 80 does not protrude outwardly from the fixation body 42 when fully seated in the screw hole 72. For instance, the screw head 80 can be flush with the outer surface 59 of the fixation body 42, though the screw head 80 could alternatively be inwardly recessed or slightly outwardly protruding with respect to the outer surface 59 of the fixation body 42 as desired. As described above, at least a portion of the inner surfaces 76 can be threaded so as to threadedly mate with the corresponding outer surface 78 of the respective screw head. Alternatively or additionally, at least a portion of the inner surfaces 76 can be unthreaded such that the screw head 80 compresses the fixation body 42 toward the underlying bone as the fastener 44 is driven through the screw hole 72 and into the bone.

Of course, the screw hole 72 could assume one of numerous configurations, such that the inner surface 76 can be beveled straight, or rounded at any desired radius, for instance approximately 3.6 mm. Alternatively still, the inner surface 76 need not be beveled, and can extend laterally in a direction parallel to the outer surface of the screw head 80.

Figure 14:
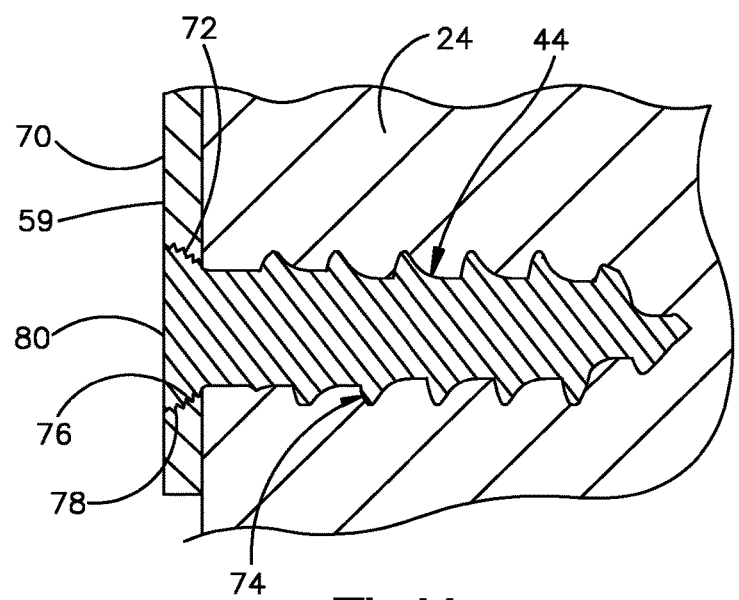
FIG. 14 is a sectional elevation view of the fixation device illustrated in FIG. 12, implanted in the manner illustrated in FIG. 10, and taken along line 14-14 of FIG. 10 to show the fixation of the device to underlying bone.

As illustrated in FIG. 6, at least one or more up to all of the inner surfaces 76 can be smooth and flat, and the corresponding outer surfaces 78 can likewise be smooth. Accordingly, when the threaded shaft 75 of the screw 74, which extends out from the head 80, is driven through the screw hole 72 and into the underlying bone, for instance bone 24, the outer surface 78 can compress against the inner surface 76, thereby compressing the attachment locations 70, and thus the bone fixation body 42, against the underlying bone. Alternatively, as illustrated in FIG. 14, the inner and outer surfaces 76 and 78 can be threaded, such that the threaded heads 80 are configured to threadedly mate with the attachment locations 70. Accordingly, when the threaded shaft 75 is driven through the screw hole 72 and into the underlying bone, for instance bone 24, the outer surface 78 can threadedly mate with the inner surface 76, thereby securing the attachment locations 70, to the underlying bone without compressing the attachment locations against the underlying bone.

Referring now to FIGS. 15A-17B, the fasteners 44 can be constructed in accordance with any suitable embodiment as desired. For instance, one or more of the fasteners 44 up to all of the fasteners 44 can include a body 100 that includes a shaft 108 and a stop member 110. The body 100 defines a proximal end 100a and a distal end 100b opposite the proximal end 100a and spaced from the distal end 100b in a proximal direction. The shaft 108, and thus the body 100, is elongate along a central axis 102 from the proximal end 100a to the opposed distal end 100b. The fasteners 44 can further include a head 104 that extends out from the proximal end 100a at least along a radial direction that is perpendicular to the central axis 102. The head 104 can also extend out from the proximal end 100a in the proximal direction. The head 104 can be configured to engage a driving instrument, such as a screwdriver, that, in turn, is configured to apply a torsional force to the fixation member 44 about the central axis 102. For instance, the head 104 can define any suitable drive interface 106 that is configured to engage the driving instrument. The head 104 can define an outer surface 104a that faces generally in the proximal direction, and thus away from the shaft 108. The drive interface 106 can be configured as a recess that extends into the outer surface 104a, such as a cruciform, a flat recess, a star shaped socket, a hex-shaped recess, a triangular recess, or any suitable alternatively constructed interface as desired. Alternatively or additionally, a radially outer surface of the head 104 that faces generally away from the central axis 102 can define the drive interface as desired.

The shaft 108 can define a proximal shaft end 108a and a distal shaft end 108b spaced from the proximal shaft end 108a along the central axis 102 in a distal direction that is opposite the proximal direction. The distal shaft end 108b can coincide with the distal end 100b of the body 100. The distal shaft end 108b can define a tip, which can include cutting flutes as desired. In one example, the fastener 44 can be self-tapping. At least a portion of an outer surface of the shaft 108 can be threaded, such that the shaft 108 can define at least one external helical thread 112. The shaft 108 is sized to be inserted through the screw hole 72 and driven into the underlying bone, which can be the mandible or the maxilla. For instance, the fastener 44 can be rotated about the central axis 102 so as to drive the threaded shaft 108 into the underlying bone. The stop member 110 extends radially out away from the central axis 102, and is configured to abut the bone fixation body 42 at the respective attachment location 70, and thus at the respective valley 30. For instance, the stop member 110 can be configured to abut the inner surface 76 of the screw hole 72. The stop member 110 is disposed between the shaft 108 and the head 104 along the central axis 102. Accordingly, the body 100 defines a neck 114 that is disposed between the head 104 and the stop member 110. The neck 114 is recessed with respect to at least the head 104 along an radially inward direction toward the central axis. The neck 114 can be further recessed with respect to at least a portion up to an entirety of the stop member 110 in the radially inward direction. The head 104 can extend radially outward with respect to the stop member 110, the stop member 110 can extend radially outward with respect to the head 104, or the head 104 and stop member 110 can extend radially outward the same distance as desired.

In one example, an outer surface of the stop member 110 can be threaded, such that the stop member 110 defines at least one external helical thread 116. The stop member 110 can be configured to be inserted into the screw hole 72, such that the at least one helical thread 116 threadedly purchases with the inner surface 76 of the screw hole 72. The helical thread 112 of the shaft 108 can define a first pitch, and the helical thread 116 of the stop member 110 can define a second pitch that is equal to the first pitch. Accordingly, the stop member 110 can advance in the screw hole 72 at the same rate that the shaft 108 advances in the underlying bone. It should be appreciated that the first pitch can alternatively be greater than the second pitch, such that the shaft 108 advances in the underlying bone at a rate greater than the rate at which the stop member 110 advances in the screw hole 72, thereby creating compression of the bone fixation body 42 against the underlying bone. In one example, the at least one helical thread 116 of the stop member 110 can be a double lead thread, or any suitable alternative thread as desired. At least a portion of the outer surface of the stop member 110 can be tapered in the radially inward direction toward the central axis 102 as the outer surface extends in the distal direction. For instance, the outer surface of the stop member 110 can be conical in shape. Likewise, the inner surface 76 of the screw hole 72 can be conical. Accordingly, the stop member 110 can be inserted into the screw hole 72 in the distal direction until abutment between the stop member 110 and the inner surface 76 prevents further movement of the fastener 44 with respect to the bone fixation body 42 in the distal direction. It should be appreciated, as illustrated in FIG. 16A, that the bone fixation body 42 can be placed against the underlying bone 24, for instance at the attachment location 70. Next, as illustrated in FIG. 16B, the shaft 108 can be driven through the screw hole 72 and into the underlying bone 24 until the stop member 110 threadedly mates with the inner surface 76, thereby fixing the plate body 42 at a location against the underlying bone 24. Alternatively, as illustrated in FIG. 16C, the plate body 42, at least the attachment location 70 up to an entirety of the plate body 42 can be spaced from the underlying bone 24 when the stop member 120 threadedly mates with the inner surface 76. Thus, at least a portion of the plate body 42 up to an entirety of the plate body 42 can be fixed at a location spaced from the underlying bone 24.

With continuing reference to FIGS. 15A-17, the body 100 can define a recess 101 between the head 104 and the stop member 110. The recess 101 can be sized to receive a respective securement device 23 between the head 104 and the stop member 110. The recess can define a distance along a direction parallel to the central axis 102 in a range from and including approximately 0.2 mm to approximately 6 mm. For instance, the range can be from and including approximately 0.75 mm to approximately 6 mm. For example, the distance can be approximately 1 mm. The head 104 can define a cross-sectional dimension along a direction perpendicular to the central axis 102 that is in a range from and including approximately 2 mm to approximately 9 mm. For instance, head 104 can define a cross-sectional dimension of approximately 4.5 mm. The cross-sectional dimension can, in one example, be a diameter. The neck 114 can define a cross-sectional dimension along a direction perpendicular to the central axis 102 that is in a range from and including approximately 1 mm to approximately 5 mm, such as approximately 2 mm to approximately 4 mm. In one example, the cross-sectional dimension of the neck 114 can be approximately 2.2 mm. The cross-sectional dimension of the neck 114 can be a diameter in one example. It should be appreciated that the above dimensions are presented by way of example only, and that the dimensions can vary as desired.

Thus, the head 104 can be spaced from the stop member 110 a distance in the proximal direction sufficient so as to receive the securement device 23. In accordance with one embodiment, the securement device 23 can be wrapped around the neck 114, so as to attach to one or more other fasteners 44. The securement device 23 can attach to one or more other fasteners 44 of the respective bone fixation body 42 in the manner described above. Alternatively or additionally, the securement device 23 can attach to one or more other fasteners 44 of the opposed fixation body 42 in the manner described above. Alternatively or additionally still, the securement device 23 can attach to one or more securement locations 82 of the respective fixation body 42 in the manner described above. Alternatively still, the securement device 23 can attach to one or more securement locations 82 of the opposed fixation body 42 in the manner described above. Thus, the neck 114 can be unthreaded and smooth as desired.

Referring now to FIGS. 18A-19, in accordance with another example, the stop member 110 of the fastener 44 can be configured as a shoulder 118 that is configured to abut the outer surface 59 of the bone fixation body 42. For instance, the shoulder 118 can define an outer cross-sectional dimension in a select direction perpendicular to the central axis 102 that is greater than the diameter of the screw hole 72 at the outer surface 59. In one embodiment, the shoulder 118 can define a distal surface 118a that is configured to face and abut the bone fixation body 42, and an opposed proximal surface 118b. The distal surface 118a can be substantially flat so as to create surface contact with the outer surface 59 of the bone fixation body 42. It should be appreciated, however, that the distal surface 118a can define any suitable size and shape as desired. Thus, during operation, the shaft 108 is threadedly driven into the underlying bone until the shoulder 118 abuts the outer surface 59 of the bone fixation body 42, such that further insertion of the shaft 108 into the underlying bone causes the shoulder 118 to apply a compressive force to the bone fixation body 42 toward the underlying bone.

As described above, the neck 114 is configured to attach to a respective securement device 23, such as a flexible wire, that fixes the fastener 44 to one or more other fasteners 44, one or more other securement locations 82, or a combination of fasteners 44 and securement locations 82. For instance, one or more securement devices 23 can otherwise be wrapped around or otherwise extend about the neck 114 as described above. Alternatively or additionally, the body 100 of the fastener 44 can define a first cross-bore 120 that extends through the neck 114 along a first direction perpendicular to the central axis 102. The body 100 can further define a second cross-bore 122 that extends through the neck 114 along a second direction that is different than the first direction. For instance, the second direction can be perpendicular to the first direction. Further, the second cross-bore 122 can intersect the first cross-bore 120. As illustrated in FIG. 19, each of the first and second cross-bores 120 and 122 can be sized to receive a respective securement device 23 so as to attach the fastener member 4 to one or more others of the fasteners 44 or to one or more of the securement locations 82 of the respective bone fixation body 42 or to the opposed bone fixation body as desired, as is described in more detail below. Each of the cross-bores 120 and 122 can receive respective different securement devices 23 or the same securement device 23 that is further coupled one or more other bone fixation members 44, or to one or more of the securement locations 82 as desired.

It should be appreciated that when the fastener 44 is attached to the bone fixation body 42 such that the stop member 110 is in abutment with the bone fixation body 42 to prevent further translation of the fastener 44 relative to the bone fixation body 42 in the distal direction as described herein, the head 104 can be spaced from the outer surface 59. As described above, the head 104 can be spaced from the soft tissue, such that during bone healing, the head 104 is positioned to reduce or prevent overgrowth of the mucosa. For instance, at least a portion of the recess 101 can be disposed between the head 104 and the outer surface 59. When the stop member 110 is disposed in the screw hole 72, the recess can be defined by the head 104 and the outer surface 59. When the stop member 110 abuts the outer surface, the recess 101 can be disposed between the head 104 and the outer surface 59, and defined by the head 104 and the stop member 110. In both cases, the head 104 can be spaced from the outer surface 59 by at least a recess, which can include a portion up to an entirety of the recess 101, alone or in combination with the stop member 110 that is in abutment with the outer surface 59. As a result, the head 104 is spaced from the soft tissue. Accordingly, during bone healing, the head 104 is positioned to reduce or prevent overgrowth of the mucosa. As a result, when the bone fixation system 20 is to be removed, the drive interfaces 106 can be exposed to the technician so as to facilitate removal of the fasteners 44 from the underlying bone.

As described above with respect to FIGS. 11-14, the bone fixation body 42 defines an offset region 71 at the side members 48 and 50 that spaces the securement locations 82 from the attachment locations 70 along the third direction. For example, the as the side members 48 and 50 extend from the respective attachment locations 70 to the respective securement locations 82, the side members extend outward along the third direction at the offset regions. In accordance with one embodiment, the side members 48 and 50 each extend along a respective first plane P1 from the attachment location 70, bend outward away from the first plane along the third direction to a respective second plane P2 at the offset region 71, and extend from the offset region 71 to the respective securement location 82. Thus, the side members 48 can extend along the first plane P1 at a location between the attachment location 70 and the offset region 71, and can extend along the second plane P2 at a location between the offset region 71 and the securement location 82. The second plane P2 can be parallel to the first plane P1, or can be angularly offset with respect to the first plane P1 as desired. It is thus appreciated that the crests 51 and the valleys 60 can define respective outer surfaces that lie in respective planes that are offset from each other along the third direction. The respective planes P1 and P2 can further be parallel with each other or angularly offset with respect to each other. Further, while the fixation body 42 can define a first offset between the first and second planes P1 and P2, the fixation body 42 can define any number of offsets between the first and second planes P1 and P2. Further, while the securement locations 82 can be aligned with each other along the longitudinal direction L when the fixation body 42 is in its neutral configuration, one or more up to all of the securement locations 82 can alternatively be out of alignment with respect to one or more up to all other ones of the securement locations 82 along the longitudinal direction. For instance, one or more up to all of the securement locations 82 can alternatively be offset with respect to one or more up to all other ones of the securement locations 82 along one or both of the lateral direction A and the transverse direction T.

Figure 13:
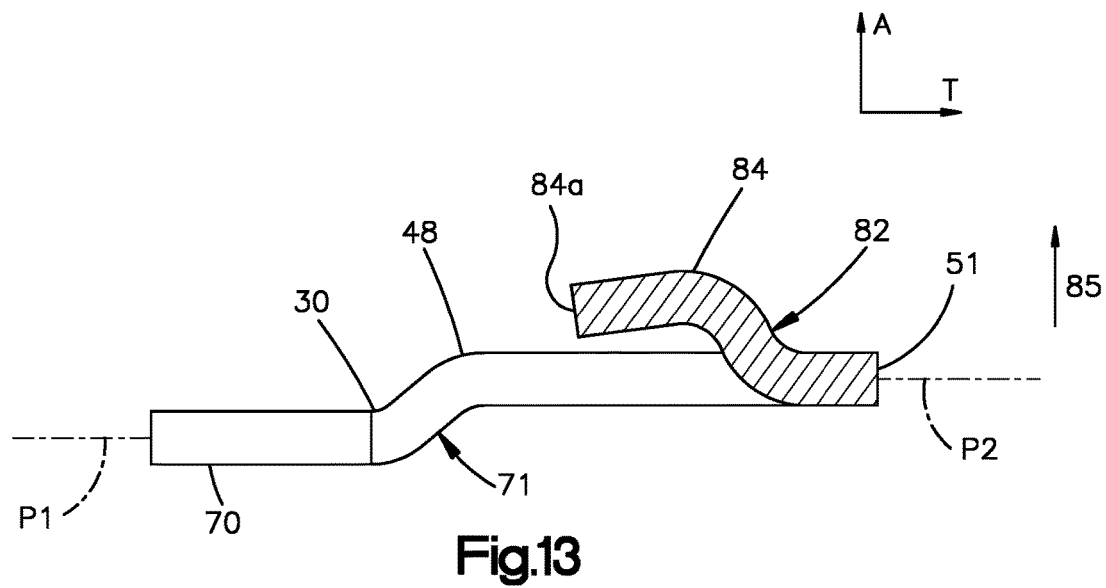
FIG. 13 is a sectional elevation view of the fixation device illustrated in FIG. 12, taken along line 13-13.

As described above, the securement locations 82 can be configured as tangs 84 that extend from the respective ones of the crests 51 along the transverse direction T, such that the tangs 84 extend toward a gap between adjacent ones of the valleys 60. It is appreciated that the tangs 84 can extend in other directions as well, as they extend along the transverse direction T. As illustrated in FIG. 13, the tangs 84 extend from the crests 51 to respective free ends 84 that are offset with respect to the respective crests 51 in an outward direction 85 that is along the third direction. It is appreciated that the securement locations 82, such as the tangs 84, are offset with respect to the attachment locations 70 in the outward direction 85. Further, the crests 51 are offset with respect to the attachment locations, and valleys 60, along the outward direction 85. The tangs 84 can further extend in an inward direction as they extend from the respective crest 51 toward their respective free end, at least along a portion of their length. The inward direction is opposite the outward direction 85, and is also along the third direction.

One or more, up to all, of the tangs 84 can also include longitudinally or laterally extending segments as well, if desired. For instance, in the illustrated embodiment, each of the tangs 84 can include the first segment 86 that extends downward along the transverse direction T from the transverse inner edge of the apex of the crest 51. The second, or spacer, segment 88 extends in the downward direction and outward along the lateral direction A from the lower end of the first segment 86. The third segment 90 can extend down in the transverse direction T from the lower end of the spacer segment 88. As illustrated in FIG. 13, the third segment 90 can further extend inward the lateral direction A, opposite the outward direction, to a distal end 84a of the tangs. Accordingly, the distal end 84a of the tang 84a can be spaced from the second plane P2 a first distance, and a proximal end of the tang 84 opposite the distal end 84a along the length of the tang 84 can be spaced from the second plane P2 a second distance greater than the first distance. The distal end 84a can be defined by the third segment 90. Thus, at least a portion up to an entirety of the third segment 90 is offset with respect to the first segment 86 in the outward direction.

As described above, a securement device, such as the securement device 23 described above, can engage the lower surface of the spacer segment 88 and laterally inner surface of the third segment 90 when fixing or stabilizing a pair of mandibular and maxillo fixation bodies 42 to each other. Alternatively or additionally, the securement device 23 can engage the laterally inner surface of the first segment 86 and the laterally outer surface of the crest 51. For instance, a wire can be wrapped around the tang 84 and/or link 46. Alternatively or additionally, an elastic band can be seated at one end between the tang 84 and the crest 51. Because securement devices 23 can be attached at multiple locations along the length of the fixation body 42, the resulting forces associated with coupling the securement devices 23 to a complementary fixation body 42 distributes the resulting forces substantially equally across the length of the fixation body 42.

Further, as illustrated in FIGS. 17 and 19, a securement device 23, such as a flexible wire, can be coupled to the neck 114 of a first at least one fastener 44 that has been driven through the screw hole 72 of a first fixation body 42 and into a respective underlying bone, such as a mandible, and can further be coupled to the neck of a second at least one fastener 44 that has been driven through the screw hole 72 of a second opposed fixation body 42' and into a respective underlying bone, such as a maxilla. The free ends of the wire can be intertwined so as to attach the first and second plates bodies 42 and 42' to each other. As illustrated in FIG. 17, the securement device 23 can extend around the necks 114 of the respective fasteners 44 as described above. Alternatively, as illustrated in FIG. 19, the securement device 23 can extend through one or both of the cross-bores 120 and 122 in the manner described above. In accordance with one embodiment, the first at least one fastener 44 of the first fixation body 42 can be configured as a pair of fasteners 44. Similarly, the at least one fastener 44 of the second fixation body 42' can be configured as a pair of fasteners 44. Thus, the securement device 23 can extend along the longitudinal direction L across at least a pair of fasteners 44 of the first fixation body 42, and can extend along the longitudinal direction L across at least a pair of fasteners of the second fixation body 42'. The fixation system 20 can include as many securement devices 23 as desired. For instance, a pair of securement devices 23 can be coupled to the necks 114 of the same fasteners 44, such that adjacent securement devices 23 of the fixation system 20 can overlap each other and share at least one fastener from each of the first and second fixation bodies 42 and 42'. Alternatively, the adjacent securement devices 23 can be spaced apart from each other so that none of the fasteners 44 to which the adjacent securement devices 23 are coupled are in common to each other.

Thus, it should be appreciated that fixation bodies can be provided in accordance with multiple embodiments. Therefore, a kit can be provided that includes a plurality of fixation devices, or portions thereof, including fixation bodies constructed in accordance with all or a portion of any of the embodiments described herein. For example, the kit can include one or more fixation bodies 42 or 42', having different numbers of links, different dimensions, such as overall length, link width, height, and lateral thickness, and differently configured links (for instance differently configured side members 48, 48', 50, and 50', securement locations 82, 82', and 96, and/or auxiliary links 92). Therefore, the fixation bodies in a kit can have one or more varying characteristic such as size and/or shape. For instance, a first kit can be provided having one or more fixation bodies whose components, for instance the links and/or the securement locations, are of a first size or shape, and other fixation bodies whose components are of a second size or shape different than the first size or shape. Thus, the kit can accommodate multiple maxillo-mandibular fixation procedures involving substantial anatomical variability. In one embodiment, each of the bone fixation bodies 42 and 42' can include at least two attachment locations 70 and at least one securement location 82. One or more fixation bodies can be attached to the mandible, and one or more opposed fixation bodies 42' can be attached to the maxilla.

According to another embodiment, methods are provided for implanting the various embodiments of the fixation device 40. Generally, the methods include the steps of adjusting an orientation (e.g., directional or angular) of the fixation device 40 depending on the anatomy of the underlying bone structure. For instance, a maxillo fixation device will be vertically inverted with respect a mandibular fixation device. It is to be understood that certain steps of the methods described herein can be omitted, combined, performed simultaneously, or performed in a different order. In this regard, it should be appreciated that the maxillo-mandibular fixation devices of the type described above can be provided as a kit that is configured to be implemented for the purposes of maxillo-mandibular fixation using the methods described below.

According to one method of providing fixation to a bone or bone segments of a mandible, a first fixation device such as the fixation device 40 may be adapted by imparting a curvature as desired to correspond to the dental arch. For instance, before or after attaching the fixation body 42 to the first and second bone segments, the fixation body 42 can be flexed so as to move one or more of the crests in the lateral direction A with respect to one or more others of the crests and valleys. Alternatively or additionally, the fixation body 42 can be flexed so as to move one or more of the valleys in the lateral direction A with respect to one or more others of the crests and valleys. Thus, the fixation body 42 can be flexed to conform to the dental arch. Alternatively and additionally, the fixation body 42 can be flexed so as to rotate the bone segments with respect to each other, thereby aligning the first and second bone segments with each other during fracture reduction. The fixation device 40 can further be extended or compressed in the longitudinal direction and/or the transverse direction to align the screw holes 72 with a desired fixation location on the underlying bone. Thus the configuration of the fixation body 42 may be adapted to achieve the proper shape and fit for a bone fixation.

The fixation body 42 can be implanted by inserting the fasteners 44 into the underlying bone. For instance, the fasteners 44 can be driven through respective ones of the screw holes 72 and into the mandible, in the manner described above, on opposite sides of the fracture prior. The plate body 42 can then be flexed and deformed such that respective ones of the side members 48 and 50 are brought toward each other, thereby bringing the bone segments on opposite sides of the fracture toward each other, thus reducing the fracture. The deformed plate body 42 can provide a compression force that can at least approximate, and in some instances fully reduce, the fracture. It should thus be appreciated that the fracture in the mandible can be approximated or fully reduced before or after the fixation body 42 has been attached to the mandible. Whether the fracture has been approximated or reduced before or after the fixation body 42 has been attached to the mandible, the deformed plate body 42 can maintain the approximation or reduction. Alternatively or additionally, securement members 23 can be attached to the fasteners 44 in the manner described above at opposite sides of the fracture. Accordingly, the securement members 23, alone or in combination with the deformed plate body 42, can at least approximate, and in some instances fully reduce, the fracture. In one embodiment, the fracture can be approximated or reduced prior to attaching the securement members 23 to the fixation members 44. Thus, the securement members can maintain the fracture in the approximated or reduced configuration. In another embodiment, tension can be induced in the fixation member 44, such that the securement members 23 apply a force to the fixation members 44 that draws the side walls 48 and 50 toward each other, thereby approximating or reducing the fracture. It should thus be appreciated in certain examples that the bone fixation system 20 can reduce or approximate the fracture after fixing the plate body 42 to the underlying bone. The fracture can thus be approximated or reduced prior to attaching the plate body 42 to the underlying bone, after attaching the plate body to the underlying bone, for instance by deforming the plate body, and after the plate body has been deformed, for instance by inducing tension in the securement members 23.

Next, a second fixation device 40 can be implanted in a second bone structure that is to be fixed with respect to the bone structure that underlies the first fixation body 40. For instance, a second fixation body 42 can be implanted into the maxilla in the manner described above, but in an orientation that is vertically inverse with respect to the first fixation device 40. It should be appreciated that either the first and/or second fixation device is implanted over a fracture such that the device(s) attach a first bone segment to a second bone segment that has been fractured from the first bone segment.

Once the first and second fixation bodies are implanted into the underlying bone structure, the securement devices 23 are attached to the securement locations of the first and second fixation bodies. In a preferred embodiment, the securement devices 23 are attached between two vertically aligned, or substantially aligned, crests 51. It should be appreciated that the crests 51 of each fixation body can define the shortest vertical distance between the fixation bodies 40, thereby allowing for a securement device 23 that has a short length between the fixation bodies 40.

Thus, referring again to FIGS. 10-19 generally, the method can include the step of bringing the first and second bone segments, disposed on opposite sides of the fracture, together so as to approximate the fracture. The method can further include the step of placing the bone fixation body 42 over the first and second bone segments, such that at least a first one of the bone fixation holes 72 is aligned with the first bone segment and at least a second one of the bone fixation holes 72 is aligned with the second bone segment. The bone fixation body 42 can be placed adjacent, for instance against, the mucosa that is thus disposed between the bone fixation body 42 and the underlying bone segment. Next, the head of the fastener 44 can be engaged, for instance by a driving member, and a torsional force can be imparted to the head of the fastener 44 so as to drive the shaft of a fastener 44 through one of the bone fixation holes 72 and into the aligned bone segment. The torsional force can be discontinued after the stop member 110 has abutted the bone fixation body 42, such that head is spaced from the bone fixation body 42 by the recess 101. It should be appreciated that the torsional force can continue to be applied beyond the moment that the stop member 110 has abutted the bone fixation body 42, for instance, when compressing the fixation body 42 against the mandible. Next, a securement device 23 can be inserted into the recess 101, and coupled to the neck 114. For instance the securement device 23 can be wrapped around the neck 114. Alternatively, the securement device 23 can be inserted through at least one of the cross-bores 120. As described above, the torsional force can be discontinued before the fracture is reduced, such that flexing the bone fixation body 42 can bring the first and second bone segments together. Alternatively, the fracture can be reduced prior to placing the bone fixation body 42 adjacent the underlying bone.

The illustrated embodiments are directed to a bone fixation system that may be implanted to assist in repairing a fractured bone. The fixation system has particular utility as mandibular or maxillo fixation system, which benefits from accurate anatomical shape and fit.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. Moreover, any of the embodiments described above can incorporate any structures or features of any of the other embodiments described above, as desired. Those skilled in the relevant art, having the benefit of the teachings of this specification, may effect numerous modifications to the invention as described herein, and changes may be made without departing from the spirit and scope of the invention as defined by the appended claims.

What is claimed:

1. A bone fixation body, comprising:
a plurality of links spaced from each other along a first direction, the links defining respective crests and valleys offset from each other along a second direction that is perpendicular to the first direction, and side members that extend between the crests and valleys, such that at least some of the links, in combination, define a plurality of securement locations and a plurality of attachment locations that are spaced from each other at least along the first direction, wherein the side members each define an offset region that offsets the securement locations from the attachment locations along a third direction that is substantially perpendicular to each of the first and second directions,
wherein the attachment locations are configured to receive fasteners therethrough and into an underlying jaw bone so as to attach the bone fixation body to the underlying jaw bone, and wherein the securement locations are configured to engage with a respective securement device that secures the fixation body to complementary securement locations of a second fixation body.

2. The bone fixation body as recited in claim 1, wherein at least some of the attachment locations and the securement locations are aligned with each other with respect to the first direction.

3. The bone fixation body as recited in claim 1, wherein at least some of the securement locations and the attachment locations are offset from each other along the second direction.

4. The bone fixation body as recited in claim 1, wherein when the fasteners are inserted into the jaw bone at respective ones of the attachment locations, the attachment locations are disposed closer to the jaw bone along the third direction than a distance that the securement locations are spaced from the jaw bone along the third direction.

5. The bone fixation body as recited in claim 1, wherein as the side members extend from the respective attachment locations to the securement locations, the side members each extend along a respective first plane from the attachment location, bend outward away from the first plane along the third direction to a respective second plane that is parallel to the first plane, and extend in the second plane to the respective securement locations.

6. The bone fixation body as recited in claim 1, wherein the side members, the securement locations, and the attachment locations are monolithic with each other.

7. The bone fixation body as recited in claim 1, wherein the crests and valleys define respective outer surfaces that lie in respective planes that are offset from each other along the third direction and are parallel with each other.

8. The bone fixation body as recited in claim 1, wherein the securement locations comprise tangs that extend from the respective ones of the crests along a direction from the crests toward the valleys.

9. The bone fixation body as recited in claim 8, wherein the tangs extend from the crests to respective free ends that are offset with respect to the respective crests in an outward direction that is along the third direction.

10. The bone fixation body as recited in claim 9, wherein the crests are offset with respect to the valleys in the outward direction.

11. The bone fixation body as recited in claim 10, wherein the tangs each extend in an inward direction opposite the outward direction in a direction toward their respective free end.

12. The bone fixation body as recited in claim 1, wherein the bone fixation body is movable from a first configuration to a flexed configuration, wherein the first direction is a straight longitudinal direction when the fixation body is in the first configuration, and the first direction is curved when the fixation body is in the flexed configuration.

13. The bone fixation body as recited in claim 1, wherein the attachment locations comprise threaded bone fixation holes configured to threadedly mate with threaded heads of the fasteners.

14. The bone fixation body as recited in claim 1, wherein the attachment locations define bone fixation holes, and the attachment locations are configured to be compressed against the jaw bone when the fasteners are driven through the bone fixation holes and into the jaw bone.

15. The bone fixation body as recited in claim 1, wherein the bone fixation body is shaped in a wave-form.

16. The bone fixation body as recited in claim 1, wherein individual ones of the crests each support a respective one of the securement locations.

17. The bone fixation body as recited in claim 16, wherein individual ones of the valleys each define a respective one of the attachment locations.

18. The bone fixation body as recited in claim 1, wherein one or more of the valleys each support a respective one of the securement locations, and one or more of the valleys each define a respective one of the attachment locations.

* * * * *